US011694769B2

(12) United States Patent
Shan et al.

(10) Patent No.: US 11,694,769 B2
(45) Date of Patent: Jul. 4, 2023

(54) SYSTEMS AND METHODS FOR DE NOVO PEPTIDE SEQUENCING FROM DATA-INDEPENDENT ACQUISITION USING DEEP LEARNING

(71) Applicant: BIOINFORMATICS SOLUTIONS INC., Waterloo (CA)

(72) Inventors: Baozhen Shan, Waterloo (CA); Ngoc Hieu Tran, Waterloo (CA); Ming Li, Waterloo (CA); Lei Xin, Waterloo (CA); Rui Qiao, Waterloo (CA); Xin Chen, Waterloo (CA); Chuyi Liu, Waterloo (CA)

(73) Assignee: BIOINFORMATICS SOLUTIONS INC., Waterloo (CA)

( * ) Notice: Subject to any disclaimer, the term of this patent is extended or adjusted under 35 U.S.C. 154(b) by 1232 days.

(21) Appl. No.: 16/226,575

(22) Filed: Dec. 19, 2018

(65) Prior Publication Data

US 2019/0147983 A1  May 16, 2019

Related U.S. Application Data

(63) Continuation-in-part of application No. 16/037,949, filed on Jul. 17, 2018, now Pat. No. 11,573,239.
(Continued)

(51) Int. Cl.
*G01N 33/48* (2006.01)
*G01N 33/50* (2006.01)
(Continued)

(52) U.S. Cl.
CPC ........ *G16B 40/10* (2019.02); *G01N 33/6818* (2013.01); *G01N 33/6848* (2013.01);
(Continued)

(58) Field of Classification Search
CPC ........ G16B 40/10; G06N 3/02; H01J 49/0036
See application file for complete search history.

(56) References Cited

U.S. PATENT DOCUMENTS

2017/0131247 A1* 5/2017 Gazis ................. G01N 30/8617
2019/0205747 A1* 7/2019 Srivastava ............ G06K 9/623

FOREIGN PATENT DOCUMENTS

WO      2005/057208 A1    6/2005

OTHER PUBLICATIONS

Ott, P.A. et al. An immunogenic personal neoantigen vaccine for patients with melanoma. Nature 547, 217-221 (2017).
(Continued)

*Primary Examiner* — Russell S Negin
(74) *Attorney, Agent, or Firm* — Norton Rose Fulbright Canada LLP

(57) ABSTRACT

The present systems and methods introduce deep learning to de novo peptide sequencing from tandem mass spectrometry data, and in particular mass spectrometry data obtained by data-independent acquisition. The systems and methods achieve improvements in sequencing accuracy over existing systems and methods and enables complete assembly of novel protein sequences without assisting databases. To sequence peptides from mass spectrometry data obtained by data-independent acquisition, precursor profiles representing intensities of one or more precursor ion signals associated with a precursor retention time and fragment ion spectra representing signals from fragment ions and fragment retention times are fed into a neural network.

36 Claims, 16 Drawing Sheets

Related U.S. Application Data

(60) Provisional application No. 62/533,560, filed on Jul. 17, 2017.

(51) Int. Cl.

| | |
|---|---|
| G16B 40/10 | (2019.01) |
| H01J 49/00 | (2006.01) |
| G01N 33/68 | (2006.01) |
| G16B 30/20 | (2019.01) |
| G16B 40/20 | (2019.01) |
| G06N 3/02 | (2006.01) |

(52) U.S. Cl.
CPC .............. *G06N 3/02* (2013.01); *G16B 30/20* (2019.02); *G16B 40/20* (2019.02); *H01J 49/0036* (2013.01)

(56) References Cited

OTHER PUBLICATIONS

Muntel, J. et al. Advancing urinary protein biomarker discovery by data-226 independent acquisition on a Quadrupole-Orbitrap mass spectrometer. J. 227 Proteome Res. 14, 4752-4762 (2015).228.

Editorial. The problem with neoantigen prediction. Nat. Biotechnol. 35, 97 (2017).

Caron, E. et al. An open-source computational and data resource to analyze 234 digital maps of immunopeptidomes. eLife 4, e07661 (2015).

Bassani-Sternberg, M. et al. Direct identification of clinically relevant neoepitopes presented on native human melanoma tissue by mass spectrometry. Nat. Commun. 7, 13404 (2016).

Venable, J.D., Dong, M.Q., Wohlschlegel, J., Dillin, A. & Yates, J.R . Automated approach for quantitative analysis of complex peptide mixtures from tandem mass spectra. Nat. Methods 1, 39-45 (2004).

Röst, H.L. et al. OpenSWATH enables automated, targeted analysis of data-independent acquisition MS data. Nat. Biotechnol. 32, 219-223 (2014).

Egertson, J.D., MacLean, B., Johnson, R., Xuan, Y. & MacCoss, M.J. Multiplexed peptide analysis using data-independent acquisition and Skyline. Nat. Protoc. 10, 887-903 (2015).

Tsou, C. et al. DIA—Umpire: comprehensive computational framework for data-independent acquisition proteomics. Nat. Methods 12, 258-264 (2015).

Ting, Y.S. et al. PECAN: library-free peptide detection for data-independent acquisition tandem mass spectrometry data. Nat. Methods 14, 903-904 (2017).

Bernhardt, O. et al. Spectronaut: a fast and efficient algorithm for MRM-like 231 processing of data independent acquisition (SWATH-MS) data. 60th American 232 Society for Mass Spectometry Conference (2012).

Lin, T.Y., Goyal, P., Girshick, R., He, K. & Dollár, P. Focal loss for dense object 221 detection. arXiv:1708.02002 [cs.CV] (2017).222.

Zhang, J. et al. PEAKS DB: De novo sequencing assisted database search for 223 sensitive and accurate peptide identification. Mol. Cell. Proteomics 11, 224 M111.010587 (2012).225.

Catusse, J., Strub, J.-M., Job, C., Van Dorsselaer, A. & Job, D. Proteome-wide characterization of sugarbeet seed vigor and its tissue specific expression. Proc. Natl. Acad. Sci. U.S.A. 105, 10262-10267 (2008).

Novo, J.V.J., Pascual, J., Lucas, R.S., Romero-Rodriguez, C., Ortega, M.R., Lenz, C. & Valledor, L. Fourteen years of plant proteomics reflected in Proteomics: moving from model species and 2DE-based approaches to orphan species and gel-free platforms. Proteomics 15, 1089-1112 (2015).

Maggon, K. Monoclonal antibody "gold rush". Curr. Med. Chem. 14, 1978-1987 (2007).

Tran., N.H., Rahman, M.Z., He, L., Xin, L., Shan, B.Z. & Li, M. Complete de novo assembly of monoclonal antibody sequences. Scientific Reports 6, 31730 (2016).

LeCun, Y., Bengio, Y. & Hinton, G. Deep learning. Nature 521, 436-444 (2015).

Ciresan, D., Giusti, A., Gambardella, L.M. & Schmidhuber, J. Deep neural networks segment neuronal membranes in electron microscopy images. In Proc. Advances in Neural Information Processing Systems 25, (2012).

Krizhevsky, A., Sutskever, I. & Hinton, G. ImageNet classification with deep convolutional neural networks. In Proc. Advances in Neural Information Processing Systems 25, (2012).

Hinton, G. et al. Deep neural networks for acoustic modeling in speech recognition: the shared views of four research groups. IEEE Signal Processing Magazine. 29, 82-97 (2012).

Sutskever, I., Vinyals, O. & Le, Q. Sequence to sequence learning with neural networks. In Proc. Advances in Neural Information Processing Systems 27, 3104-3112 (2014).

Glorot, X., Bordes, A. & Bengio, Y. Deep sparse rectifier neural networks. Proceedings of the Fourteenth International Conference on Artificial Intelligence and Statistics (AISTATS), (2011).

Zhou, J. & i royanskaya, O.G. Predicting effects of noncoding variants with deep learning based sequence model. Nat, Methods 12, 931-934 (2015).

Wang, S., Sun, S., Li, Z., Zhang, R. & Xu, JB. Accurate de novo prediction of protein contact map by ultra-deep learning model. PLoS Comput. Biol. 13, e1005324 (2017).

Hochreiter, S. & Schmidhuber, J. Long short-term memory. Neural Computation 9, 1735-1780 (1997).

Karpathy, A. & Li, F.F. Deep visual-semantic alignments for generating image description. IEEE Conference on Computer Vision and Pattern Recognition (CVPR), 3128-3137 (2015).

Vinyals, O., Toshev, A., Bengio, S. & Erhan, D. Show and tell: a neural image caption generator. IEEE Conference on Computer Vision and Pattern Recognition (CVPR), 3156-3164 (2015).

Mikolov, T., Sutskever, I., Chen, K., Corrado, G. & Dean, J. Distributed representations of words and phrases and their compositionality. In Proc. Advances in Neural Information Processing Systems 26, 3111-3119 (2013).

LeCun, Y. et al. Backpropagation applied to handwritten zip code recognition. Neural Comput. 11, 541-551 (1989).

Grosche A. et al. The proteome of native adult Muller Glial cells from murine retina. Mol. Cell. Proteomics 15, 462-480 (2016).

Marza, E. et al. Genome-wide screen identifies a novel p97/CDC-48-dependent pathway regulating ER-stress-induced gene transcription. EMBO Rep. 16, 332-340 (2015).

Pettersen, V.K., Mosevoll, K.A., Lindemann, P.C. & Wiker, H.G. Coordination of metabolism and virulence factors expression of extraintestinal pathogenic *Escherichia coli* purified from blood cultures of patients with sepsis. Mol. Cell. Proteomics 15, 2890-2907 (2016).

Hu, H. et al. Proteome analysis of the hemolymph, mushroom body, and antenna provides novel insight into honeybee resistance against varroa infestation. J. Proteome Res., 15, 841-854 (2016).

Hebert A.S. et al. The one hour yeast proteome. Mol Cell. Proteomics. 13, 339-347 (2014).

Cypryk, W. et al. Proteomic and bioinformatic characterization of extracellular vesicles released from human macrophages upon influenza A virus infection. J. Proteome Res., 16, 217-227 (2017).

Inglese, P. et al. Deep learning and 3D-DESI imaging reveal the hidden metabolic heterogeneity of cancer. Chem. Sci., (2017).

Davis, J. & Goadrich, M. The relationship between Precision-Recall and ROC curves. Proceedings of the 23rd International Conference on Machine Learning, 233-240 (2006).

Kingma, D.P. & Ba, J. Adam: a method for stochastic optimization. arXiv:1412.6980.

Kall, L., Cantebury, J.D., Weston, J., Noble, W.S. & MacCoss, M.J. Semi-supervised learning for peptide identification from shotgun proteomics datasets. Nat. Methods 4, 923-925 (2007).

Paiva, A.L., Oliveira, J.T., de Souza, G.A. & Vasconcelos, I.M. Label-free proteomics reveals that Cowpea severe mosaic virus transiently suppresses the host leaf protein accumulation during the compatible interaction with Cowpea (*Vigna unguiculata* [L.] Walp.). J. Proteome Res., 15, 4208-4220 (2016).

(56) References Cited

OTHER PUBLICATIONS

Nevo, N. et al. Impact of cystinosin glycosylation on protein stability by differential dynamic stable isotope labeling by amino acids in cell culture (SILAC). Mol. Cell Proteomics, 16, 457-468 (2017).
Cassidy, L., Prasse, D., Linke, D., Schmitz, R.A. & Tholey, A. Combination of bottom-up 2DLC-MS and semi-top-down GelFree-LC-MS enhances coverage of proteome and low molecular weight short open reading frame encoded peptides of the Archaeon Methanosarcina mazei. J. Proteome Res., 15, 3773-3783 (2016).
Reu, D.R. et al. Large-scale reduction of the Bacillus subtilis genome: consequences for the transcriptional network, resource allocation, and metabolism. Genome Res., 27, 289-299 (2017).
Petersen, J.M. et al. Chemosynthetic symbionts of marine invertebrate animals are capable of nitrogen fixation. Nat. Microbiol., 2, 16195 (2016).
Seidel, G. et al. Quantitative global proteomics of Yeast PBP1 deletion mutants and their stress responses identifies glucose metabolism, mitochondrial, and stress granule changes. J. Proteome Res., 16, 504-515 (2017).
International Search Report and Written Opinion issued in International Application No. PCT/CA2018/051628, dated Apr. 10, 2019.
Tran et al., "Deep Omics", Proteomics Journal, vol. 18, Issue 2, Jan. 24, 2018, pp. 1 to 5.
Tran et al., "Protein Identification with Deep Learning: From ABC to XYZ", arXiv: 1710.02765, 2017, pp. 1 to 16.
Tran et al., "De Novo Peptide Sequencing by Deep Learning", Proceedings of the National Academy of Sciences (PNAS), vol. 114, No. 31, Aug. 1, 2017, pp. 8247-8252.
Demichev et al., "DIA-NN: Deep Neural Networks Substantially Improve the Identification Performance of Data-Independent Acquisition (DIA) in Proteomics", bioRxiv preprint first posted online Mar. 15, 2018, pp. 1 to 16. doi: http://dx.dio.org/10.1101/282699.
Seidler et al., "De Novo Sequencing of Peptides by MS/MS", Proteomics Journal, vol. 10, Issue 4, Feb. 18, 2010, pp. 634 to 639.
Rahman et al., "In-Depth Proteomics Analysis Using a timsTOF with the PASEF Method and Deep Learning", ASMS 2018, thP388, Jun. 7, 2018.
Johnson, R.S. & Biemann, K. The primary structure of thioredoxin from Chromatium vinosum determined by high-performance tandem mass spectrometry Biochemistry 26, 1209-1214 (1987).
Martin-Visscher, L.A., van Belkum, M.J., Gameau-Tsodikova, S., Whittal, R.M., Zheng, J., McMullen, L.M., & Vederas, J.C. Isolation and characterization of camocyclin a, a novel circular bacteriocin produced by Camobacterium maltaromaticum UAL307. Appl. Environ. Microbiol. 74, 4756-4763 (2008).
Hatano, N. & Hamada, T. Proteome analysis of pitcher fluid of the carnivorous plant Nepenthes alata. J. Proteome Res. 7, 809-816 (2008).
Mata, C.I. et al. In-depth characterization of the tomato fruit pericarp proteome. Proteomics, 17, 1-2 (2017).
Srivastava, N., Hinton, G., Krizhevsky, A., Sutskever, I. & Salakhutdinov, R. Dropout: a simple way to prevent neural networks from overfitting. J. Mach. Learn. Res. 15, 1929-1958 (2014).
Taylor, J.A. & Johnson, R.S. Sequence database searches via de novo peptide sequencing by tandem mass spectrometry. Rapid Commun. Mass Spectrom. 11, 1067-1075 (1997).
Taylor, J.A. & Johnson, R.S. Implementation and uses of automated de novo peptide sequencing by tandem mass spectrometry. Anal. Chem. 73, 2594-2604 (2001).
Chen, T., Kao, M.Y., Tepel, M., Rush, J. & Church, G.M. A dynamic programming approach to de novo peptide sequencing via tandem mass spectrometry J. Comput. Biol. 8, 325-337 (2001).
Dancik, D., Addona, T.A., Clauser, K.R., Vath, J.E. & Pevzner, P.A. De novo peptide sequencing via tandem mass spectrometry. J. Comp. Biol. 6, 327-342 (1999).
Ma, B., Zhang, K., Hendrie, C., Liang, C., Li, M., Doherty-Kirby, A. & Lajoie, G. Peaks: powerful software for peptide de novo sequencing by tandem mass spectrometry. Rapid Commun. Mass Spectrom. 17, 2337-2342 (2003).
Zhang, Z. De novo peptide sequencing based on a divide-and-conquer algorithm and peptide tandem spectrum simulation. Anal. Chem. 76, 6374-6383 (2004).
Frank, A. & Pevzner, P.A. PepNovo: de novo peptide sequencing via probabilistic network modeling. Anal. Chem. 77, 964-973 (2005).
Fischer, B., Roth, V., Roos, F., Grossmann, J., Baginsky, S., Widmayer, P., Gruissem, W. & Buhmann, J.M. NovoHMM: a hidden Markov model for de novo peptide sequencing. Anal. Chem. 77, 7265-7273 (2005).
DiMaggio, P.A. & Floudas, C.A.: De novo peptide identification via tandem mass spectrometry and integer linear optimization. Anal. Chem. 79, 1433-1446 (2007).
Mo, L., Dutta, D., Wan, Y. & Chen, T. MSNovo: a dynamic programming algorithm for de novo peptide sequencing via tandem mass spectrometry. Anal. Chem. 79, 4870-4878 (2007).
Chi, H. et al. pNovo: de novo peptide sequencing and identification using HCD spectra. J. Proteome Res. 9, 2713-2724 (2010).
Jeong, K., Kim, S. & Pevzner, P.A. UniNovo: a universal tool for de novo peptide sequencing. Bioinformatics 29, 1953-1962 (2013).
Chi, H. et al. pNovo+: de novo peptide sequencing using complementary HCD and ETD tandem mass spectra. J. Proteome Res. 12, 615-625 (2013).
Ma, B. Novor: real-time peptide de novo sequencing software. J. Amer. Soc. Mass Spectrom. 26, 1885-1894 (2015).
Tsou, C. et al., DIA-Umpire: Comprehensive Computational Framework for Data-Independent Acquisition Proteomics, Nature Methods, vol. 12, No. 3, Nature America, Mar. 2015.
Kim, S. & Pevzner, P.A. MS-GF+ makes progress towards a universal database search tool for proteomics. Nat. Commun. 5, 5277 (2014).
Bandeira, N., Pham, V., Pevzner, P., Arnott, D. & Lill, J.R. Automated de novo protein sequencing of monoclonal antibodies. Nat. Biotechnol. 26, 1336-1338 (2008).
Guthals, A., Clauser, K.R., Frank, A.M., & Bandeira, N. Sequencing-grade de novo analysis of MS/MS triplets (CID/HCD/ETD) from overlapping peptides. J. Proteome Res. 12, 2846-2857 (2013).
Ma, B. & Johnson, R. De novo sequencing and homology searching. Mol. Cell Proteomics 11, O111.014902. (2012).
Steen, H. & Mann, M. The abc's (and xyz's) of peptide sequencing. Nat. Rev. Mol. Cell Biol., 699-711 (2004).
Alipanahi, B., Delong, A., Weirauch, M.T. & Frey, B.J. Predicting the sequence specificities of DNA- and RNA-binding proteins by deep learning. Nat. Biotechnology 33, 831-838 (2015).
Zhang, Y. et al. Tissue-based proteogenomics reveals that human testis endows plentiful missing proteins. J. Proteome. Res. 14, 3583-3594 (2015).

\* cited by examiner (a)

(b)

SYSTEMS AND METHODS FOR DE NOVO PEPTIDE SEQUENCING FROM DATA-INDEPENDENT ACQUISITION USING DEEP LEARNING

CROSS-REFERENCE TO RELATED APPLICATIONS

This application is a continuation-in-part of U.S. application Ser. No. 16/037,949, titled "METHODS AND SYSTEMS FOR DE NOVO PEPTIDE SEQUENCING USING DEEP LEARNING" filed Jul. 17, 2018, which claims all benefit of including priority from U.S. Provisional Application No. 62/533,560, titled "METHODS AND SYSTEMS FOR DE NOVO PEPTIDE SEQUENCING USING DEEP LEARNING" filed on Jul. 17, 2017, both of which are incorporated herein by reference.

FIELD

The claimed embodiments relates to the field of protein sequencing and, more specifically, de novo peptide sequencing using deep learning.

BACKGROUND

Proteomics research focuses on large-scale studies to characterize the proteome, the entire set of proteins, in a living organism. In proteomics, de novo peptide sequencing from tandem mass spectrometry (MS/MS) data plays the key role in the characterization of novel protein sequences. This field has been studied over the past 20 years and a number of de novo sequencing tools have been proposed such as PepNovo™, PEAKS™, NovoHMM™, MSNovo™, pNovo™, UniNovo™, Novor™, among others [6-19]. The recent "gold rush" into monoclonal antibodies has elevated the application of de novo sequencing to a new horizon. Yet computational challenges still remain as MS/MS spectra contain much noise and ambiguity that requires rigorous global optimization with various forms of dynamic programming that have been developed over the past decade.

In addition, recent developments in mass spectrometry instrumentation have led to the development of new data acquisition methods, which faces limitations in extracting quantitative information from the acquired data.

Monoclonal antibodies play important roles in therapeutic strategies due to their mechanisms of variations. However, it is such variations that also defied many attempts at developing an automated system to sequence them. Each monoclonal antibody (mAb) sequence is a novel protein that requires de novo sequencing with no resembling proteins (for the variable regions) in the databases.

SUMMARY OF THE INVENTION

De novo sequencing of a peptide from mass spectrometry data acquired by data-independent acquisition is a difficult technical endeavor as limited computing resources and processing availability limits the accuracy and practical uses of mass spectrometry data. Deep learning is used as a mechanism for providing a specific technical architecture to yield a technical improvement over alternate approaches for de novo sequencing, as mass spectrometry data is notoriously difficult to interpret because they are highly multiplexed (e.g., the links are unknown between precursor ions and fragment ions).

An improved, higher-resolution approach is described herein that utilizes a non-conventional approach to using a deep learning framework that is restructured to utilize an extra-dimensionality of DIA data (e.g., m/z and retention time) to identify co-eluting patterns of a precursor ion and its fragment ions, as well as fragment ions across multiple neighbor spectra. Accordingly, more accurate data and insights in relation to complex physical biological functions can be obtained through improved identification and determination of amino acid sequences of peptides.

As described herein in further detail in various claimed embodiments, an approach is provided for using deep learning, and in particular, neural networks, to learn (i) the 3D shapes of fragment ions along m/z and retention time dimensions, (ii) the correlation between the precursor and its fragment ions, and (iii) the peptide sequence patterns. The framework combines recurrent and beam-search mechanisms. During comparisons with other approaches, an improved accuracy is noted and tested against real-world data sets in relation to ovarian cysts, urinary tract infections, and plasma samples.

Given the complexity of analysis, computer implementation is essential in practical implementations of the claimed embodiments. Computer processors, computer memory, and input/output interfaces are provided as a system or a special purpose machine (e.g., a rack-mounted appliance residing in a healthcare data center) adapted for conducting de novo peptide sequencing. The claimed embodiments are specific technical solutions to computer problems arising in relation to conducting peptide sequencing. A neural network is maintained on associated computer memory or storage devices (e.g., in the form of software fixed on non-transitory computer readable media, hardware, embedded firmware), and trained in relation to data sets. The system or special purpose machine may interface with data repositories storing training data sets or actual data sets (e.g., from a physical mass-spectrometry machine receiving biological samples).

In some embodiments, the search space for the computer-based analysis is reduced in view of preserving finite computing resources. The outputs may be generated probability distributions, predictions, sequences, among others, and can be fixed into computer-readable media storing data sets and instruction sets. An output data structure, for example, may include a machine-interpretable or coded output of an amino acid sequence of all or part of a protein or peptide, along with metadata to characterize modifications, or reference data to databases of protein sequences. In the context of a novel sequence, a new database entry may be automatically created by issuing control signals to modify a backend database. Associated confidence scores may also be provided to indicate a level of uncertainty in relation to the prediction.

These outputs may be utilized for report generation or, in some embodiments, modifying control parameters of downstream systems or mechanisms, and a specific example area of usage includes improving personalized immunotherapy for treating cancer, as some of the embodiments described herein can be utilized for complementing and validating approaches for exome sequencing, somatic-mutation calling, and prediction of major major-histocompatibility-complex binding. Other practical approaches include the use of the outputs for improving vaccine design (e.g., malaria vaccine), as improved profiles of biological samples are provided by the approach described in various claimed embodiments.

Furthermore, improved sensitivity is possible in relation to the detection of low-abundance peptides and, in some embodiments, novel sequences that do not exist in any database may be identified.

In accordance with an aspect of the present invention, there is provided a computer implemented system for de novo sequencing of a peptide from mass spectrometry data acquired by data-independent acquisition using neural networks, the computer implemented system comprising: at least one memory and at least one processor configured to receive: a first input representing at least one precursor profile, each precursor profile representing intensities of one or more precursor ion signals associated with a precursor retention time; a second input representing a plurality of fragment ion spectra for each precursor profile, each fragment ion spectra representing: signals from fragment ions generated from an associated precursor ion, and a fragment retention time; and provide a plurality of layered computing nodes configured to form an artificial neural network for generating a probability measure for one or more candidates to a next amino acid in an amino acid sequence, the artificial neural network trained on mass spectrometry data containing retention time, a plurality of fragment ions peaks of sequences differing in length and differing by one or more amino acids; wherein the plurality of layered nodes are configured to receive a mass spectrometry spectrum data base on the first and second inputs, the mass spectrometry spectrum data representing the at least one precursor profile and the fragment ion spectra, the plurality of layered nodes comprising at least one convolutional layer for filtering mass spectrometry spectrum data to detect fragment ion peaks; and wherein the processor is configured to: receive an input prefix representing a determined amino acid sequence of the peptide, provide the mass spectrometry spectrum data to the plurality of layered nodes, identify a next amino acid based on a candidate next amino acid having a greatest probability measure based on the output of the artificial neural network and the mass spectrometry spectrum data of the peptide; update the determined amino acid sequence with the next amino acid, and generate an output signal representing a final determined sequence.

In another aspect there is provided a method for de novo sequencing of a peptide from mass spectrometry data acquired by data-independent acquisition using neural networks, the method comprising: receiving a first input representing at least one precursor profile, each precursor profile representing intensities of one or more precursor ion signals associated with a precursor retention time; receiving a second input representing a plurality of fragment ion spectra for each precursor profile, each fragment ion spectra representing: signals from fragment ions generated from an associated precursor ion, and a fragment retention time; filtering the mass spectrometry spectrum data to detect fragment ion peaks by at least one convolutional layer of a plurality of layered nodes configured to form an artificial neural network for generating a probability measure for one or more candidates to a next amino acid in an amino acid sequence; receiving a probability measure for each candidate of a next amino acid; obtaining an input prefix representing a determined amino acid sequence of the peptide; providing a mass spectrometry spectrum data based on the first and second inputs to the plurality of layered nodes; identifying a next amino acid based on a candidate next amino acid having a greatest probability measure based on the output of the artificial neural network and the mass spectrometry spectrum data of the peptide; updating the determined amino acid sequence with the next amino acid; and generating an output signal representing a final determined sequence.

Computer readable media storing machine interpretable instructions, which when executed, cause a processor to perform steps of a method described in various embodiments herein are contemplated

BRIEF DESCRIPTION OF THE FIGURES

Embodiments of the invention may best be understood by referring to the following description and accompanying drawings. In the drawings:

In FIG. 1A, precursor ions are detected from a LC-MS map (output of precursor scam MS1). The respective m/z, charge, retention time and intensity profile data are also obtained from the LC-MS map. For each detected precursor ion, its associated MS/MS spectra (i.e. for a given retention time and m/z range) are obtained and are fed into the neural networks. In FIG. 1B, for a precursor ion, 5 MS/MS spectra were selected having retention times closest to the precursor; s retention time. The ion-CNN and spectrum-CNN learn the 3D shapes of fragment ions and the correlation between the precursor profile and its associated fragment ions. The LSTM learns peptide sequence patterns in association with the spectrum-CNN. DeepNovo performs de novo sequencing in a recurrent fashion: predicting the next amino acid by conditioning on the output of previous steps.

FIG. 7A shows DeepNovo accuracy on labeled features. At amino acid level, accuracy for OC dataset is 68.1%, for UTI dataset is 65.8%, and for Plasma dataset is 63.8%. At peptide level, accuracy for OC dataset is 52.4%, for UTI dataset is 51.1%, and for Plasma dataset is 37.4%. FIG. 2B shows distribution of DeepNovo accuracy and confidence score for quality control. (• (circle) is OC, ■ (rectangle) is UTI, ▲ (triangle) is Plasma) FIG. 7C shows precursor features with peptide identifications by in-house database search or DeepNovo. For Plasma dataset, 4207 were database search only, 3466 were database search and DeepNovo, 2529 were DeepNovo only. For UTI dataset, 8931 were database search only, 12172 were database search and DeepNovo, 13604 were DeepNovo only. For OC dataset, 6477 were database search only, 9824 were database search and DeepNovo, 11829 were DeepNovo only. FIG. 7D shows DeepNovo accuracy on overlapping features in FIG. 1B. At amino acid level, accuracy for OC dataset is 89.8%, for UTI dataset is 89.8%, and for Plasma dataset is 90.0%. At peptide level, accuracy for OC dataset is 80.5%, for UTI dataset is 81.7%, and for Plasma dataset is 77.1%. FIG. 7E shows comparison of unique peptides identified by Deep-Novo, PECAN and Spectronaut from the plasma dataset, after validation. FIG. 7F shows abundance distribution of 1,143 de novo peptides identified by DeepNovo versus 1,023 database peptides identified by DeepNovo and PECAN or Spectronaut. FIGS. 7G, 7H, 7I show example of DIA specta that contains three different peptides, all of which were predicted by DeepNovo. In each figure, the fragment ions supporting the corresponding peptide are identified. In FIG. 2G, y-ion: y1, y2, y3, y4, y5, y6, y7-H2O, y7. In FIG. 2H, y-ion: y1, y2, y3, y5, y6, y7, y8, y9; b-ion: b2, b3-H2O, b3-NH3, b3, b6. In FIG. 2I, y-ion: y1, y4, y6, y8, y9, y11, y12, y13.

DETAILED DESCRIPTION

Figure 1A:
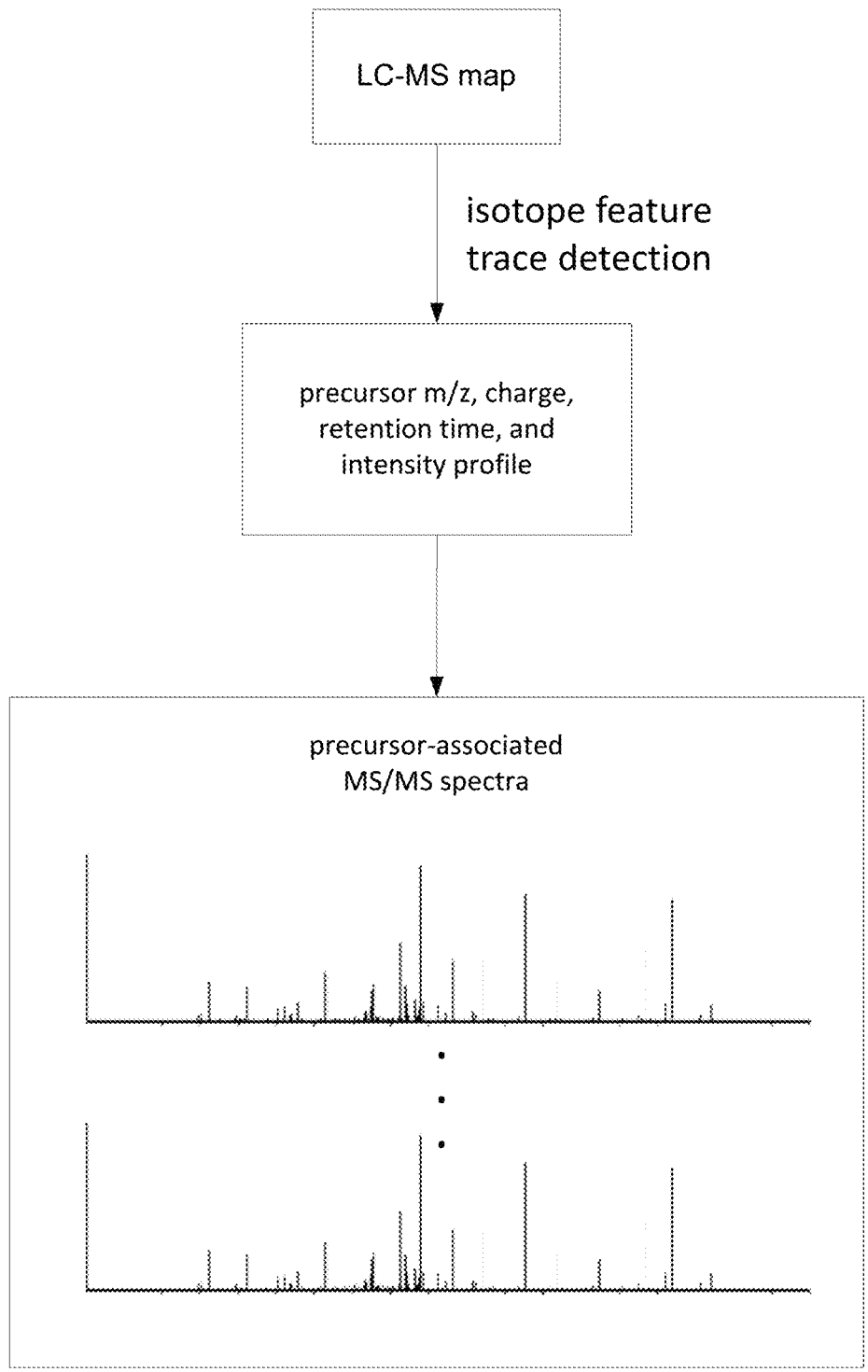
FIGS. 1A and 1B show an embodiment of a workflow of the DeepNovo system for de novo sequencing of DIA data.

De novo peptide sequencing from tandem mass spectrometry data is a technology in proteomics for the characterization of proteins, especially for new sequences such as monoclonal antibodies. The present inventors have developed a system that utilizes neural networks and deep learning to perform de novo peptide sequencing. Previously in U.S. patent application Ser. No. 16/037,949, the entire content of which is incorporated herein by reference, systems and methods were provided for de novo peptide sequencing from data acquired by data-dependent acquisition (DDA).

Presently, further developments have been made to provide systems and methods for de novo peptide sequencing of peptides from mass spectrometry data acquired by data-independent acquisition (DIA). By using neural networks to capture the signals of precursor and fragment ions across m/z, retention time, and intensity dimensions, 3-dimensional ion profiles are further integrated with peptide sequence patterns to address the problem of highly multiplexed spectra in DIA.

As used herein, "de novo peptide sequencing" refers to a method in which a peptide amino acid sequence is determined from raw mass spectrometry data. De novo sequencing is an assignment of peptide fragment ions from a mass spectrum. In a mass spectrum, an amino acid is determined by two fragment ions having a mass difference that corresponds to an amino acid. This mass difference is represented by the distance between two fragment ion peaks in a mass spectrum, which approximately equals the mass of the amino acid. In some embodiments, de novo sequencing systems apply various forms of dynamic programming approaches to select fragment ions and predict the amino acids. The dynamic programming approaches also take into account constrains, for example that a predicted amino acid sequence must have corresponding mass.

As used herein, "deep learning" refers to the application to learning tasks of artificial neural networks (ANNs) that contain more than one hidden layer. Deep learning is part of a broader family of machine learning methods based on learning data representations, as opposed to task specific algorithms. One key aspect of deep learning is its ability to learn multiple levels of representation of high-dimensional data through its many layers of neurons. Furthermore, unlike traditional machine learning methods, those feature layers are not pre-designed based on domain-specific knowledge and hence they have more flexibility to discover complex structures of the data.

Personalized immunotherapy is currently revolutionizing cancer treatment [1-4]. However, challenges remain in identifying and validating somatic mutation-associated antigens, called neoantigens, which are capable of eliciting effective anti-tumor T-cell responses for each individual. The current process of exome sequencing, somatic mutation analysis, and major histocompatibility complex (MHC) binding prediction is a long and unreliable detour to predict neoantigens that are brought to the cancer cell surface [3, 4]. This process can be complemented and validated by mass spectrometry (MS) technology [3-5]. In addition to obtaining enough tumor samples for MS analysis, the following two problems also need to be addressed: (i) sufficient sensitivity to detect low-abundance peptides and (ii) capability to discover novel sequences that do not exist in any databases. Systems and methods described herein that couples unbiased, untargeted acquisition of MS data, together with de novo sequencing allows for identification of novel peptides in human antibodies and antigens, which have been reported for immunotherapy against cancer, HIV, Ebola, and other diseases.

Mass Spectrometry

In some embodiments, the system comprises a mass spectrometer, examples of which include: tandem mass spectrometer (MS/MS) and liquid chromatography tandem mass spectrometer (LC-MS/MS). LC-MS/MS combines liquid chromatography (LC) with a tandem mass spectrometer. Mass spectrometry (MS) is an analytical technique that ionizes chemical species and sorts the ions based on their mass-to-charge ratio. A tandem mass spectrometer (MS/MS) involves two stages of mass spectrometry selection and fragmentation. MS can be applied to pure samples as well as complex mixtures. In an example MS procedure, a sample, which may be solid, liquid, or gas, is ionized, for example, by bombarding it with electrons. This causes some of the sample's molecules to break into charged fragments of various sizes and masses. For example, a 10 amino acid length peptide is fragmented between the $3^{rd}$ and $4^{th}$ amino acid, resulting in one fragment of 3 amino acids long and another fragment of 7 amino acids long. These are also referred to as b- and y-ions. These ions are then separated according to their mass-to-charge ratio and detected. The detected ions are displayed as a mass spectra of the relative abundance of detected ions as a function of the mass-to-charge ratio.

As used herein, "b-fragment ion" refers to fragment peaks on tandem mass spectrum resulting from peptide fragments extending from the amino terminus of the peptide; while "y-fragment ion" refers to fragment peaks from peptide fragments extending from the C-terminus of the peptide. In some embodiments, determining peptide sequences from the amino terminus of the peptide is referred to as the forward direction, while determining peptide sequences from the C-terminus of the peptide is referred to as the backward direction.

The overall process for mass spectrometry includes a number of steps, specifically, the ionization of the peptides, acquisition of a full spectrum (survey scan) and selection of specific precursor ions to be fragmented, fragmentation, and acquisition of MS/MS spectra (product-ion spectra). The data is processed to either quantify the different species and/or determine the peptide amino acid sequence. Since the number of ion populations generated by MS exceeds that which standard instruments can individually target for sequence analysis with a tandem mass spectrum scan, it is often necessary to control the data acquisition process and manage the limited scan speed. Data-dependent acquisition (DDA) performs a precursor scan to determine the mass-to-charge ratio (m/z) and abundance of ions eluting from the LC column at a particular time (often referred to as MS1 scan). This initial precursor scan allows for identification and screening of the most intense ion signals (precursor ions), which are then selected for subsequent fragmentation and selection in the second part of MS/MS. In MS/MS, this precursor scan is followed by isolation and fragmentation of selected peptide ions using sequence determining MS/MS scans (often referred to as MS2 scan) to generate a mass spectra. As such, DDA generates a mass spectrum based on fragment ions from a subset of peaks detected during the precursor scan.

As used herein "precursor ions" and "precursor ion signals" refer to ions and MS peak signals identified during MS1 scanning of tandem mass spectrometry.

As used herein "fragment ions" and "fragment ion signals" refer to ions and MS peak signals identified during MS2 scanning of tandem mass spectrometry.

Recent advances in mass spectrometry technology and data-independent acquisition (DIA) strategies [6, 7] allow fragmentation of all precursor ions within a certain range of m/z and retention time in an unbiased and untargeted fashion. This is contrasted with data-dependent acquisition (DDA) and selected reaction monitoring (SRM), which generates mass spectra from selected precursor ions identified in precursor scanning (MS1). In other words, mass spectra generated by DIA yield a more complete record of all peptides that are present in a sample, including those with low abundance, since a range of precursor ions are selected and fragment ions are generated from this range of precursor ions.

Mass spectrometry data is stored, for example, as a mass spectra or a plot of the ion signal as a function of the mass-to-charge ratio, a data table listing ion signal and related mass-to-charge ratio, a data string comprising pairs of ion signal and related mass-to-charge ratio, where values can be stored in corresponding data fields and data instances. The mass spectra data sets may be stored in various data structures for retrieval, transformation, and modification. Such data structures can be, for example, one or more tables, images, graphs, strings, maps, linked lists, arrays, other data structure, or a combination of same.

After a mass spectra is generated by DIA, the spectra must be decoded to extract meaningful information. However, MS/MS spectra from DIA are difficult to interpret because they are highly multiplexed. Each spectrum contains fragment ions from multiple precursor ions and the link between a precursor ion and its fragment ions is unknown. Given this highly multiplexed nature, DIA database search engines fail to achieve comparable identification power to their DDA counterparts [7-10]. The problem is even more acute for the de novo sequencing approach and no system or method has been proposed to address this. The complexity of dynamic programming or graph-based algorithms in most de novo sequencing methods for DDA increases exponentially with the multiplexity of MS/MS spectra from DIA.

In some embodiments, systems and methods are provided for de novo sequencing of DIA mass spectrometry data. In some embodiments, the systems and methods provided herein allows for interpretation of highly multiplexed mass spectrometry data. In some embodiments, the systems and methods provided herein allows for improved identification and validation of neoantigens. In some embodiments, the systems and methods provided herein allows for improved exome sequencing, somatic mutation analysis, and major histocompatibility complex (MHC) binding prediction. In some embodiments, the systems and methods provided herein allows for improved identification of novel peptides in humans antibodies and antigents. In some embodiments, the systems and methods provided herein is used in personalized immunotherapy against diseases, including but not limited to cancer, HIV, or Ebola.

Data-Independent Acquisition

A mass spectrum is often presented as a histogram-plot of intensity versus mass (more precisely, mass-to-charge ratio, or m/z) of the ions acquired from the peptide fragmentation inside a mass spectrometer. The underlying raw format (e.g. mgf) is a list of pairs of mass and intensity. Each ion is detected as a signal (such as a peak signal) having a mass-to-charge ratio and an intensity.

In some embodiments, mass spectrometry data obtained from DIA comprises precursor spectra. In one embodiment, a precursor spectrum comprises a plurality of precursor ion signals over a m/z range and at a given precursor retention time. As used herein, a "precursor spectrum" refers to a mass spectrometry spectrum generated from the MS1 scan of a tandem mass spectrometry. As used herein a "precursor feature" refers to peaks identified in the precursor spectrum. A plurality of precursor spectra can be generated over a range of precursor retention times.

In one embodiment, a precursor profile is generated from the plurality of precursor spectra. As used herein, a "precursor profile" refers to a graph, vector, table, string, arrays, or other data structure, or a combination thereof representing the signal intensities of a particular precursor ion (or a precursor ion signal having a particular mass, m/z) over a range of retention times. (see FIG. 1B, precursor profile)

In some embodiments, systems provided herein are configured to determine a precursor retention time for a precursor ion or a precursor ion signal of a particular mass, m/z. As used herein, "precursor retention time" refers to liquid chromatography retention time associated with detection of a precursor ion signal in LC-MS/MS.

In some embodiments, mass spectrometry data obtained from DIA further comprises fragment ion spectra. As used herein, a "fragment ion spectrum" refers to a mass spectrometry spectrum generated from the MS2 scan of a tandem mass spectrometry, and represents fragment ions or fragment ion signals created from subsequent fragmentation of a particular precursor ion during the second stage of a tandem mass spectrometry. In one embodiment, each fragment ion spectrum is also associated with a fragment retention time. As used herein, "fragment retention time" refers to liquid chromatography retention time associated with detection of a fragment ion signal in LC-MS/MS.

In some embodiments, the precursor spectrum and the fragment ion spectrum have the same range of m/z mass.

In some embodiments, systems and methods are provided for de novo sequencing of peptides from mass spectrometry data acquired by data-independent acquisition. In one embodiment, the system comprises a processor that uses the precursor profile and the fragment ion spectra for de novo sequencing. In one embodiment, as least one precursor profile is used, each precursor profile representing a precursor ion signal over precursor retention time. In one embodiment, as least one precursor profile is used, each precursor profile representing the intensities of a precursor ion signal over precursor retention time. In another embodiment, as least one precursor profile is used, each precursor profile representing signals from a precursor ion over precursor retention time.

In one embodiment, the system uses at most 10 fragment ion spectra for each precursor ion or precursor ion signal. In another embodiment, the system uses between 3 to 10 fragment ion spectra for each precursor ion or precursor ion signal. In yet other embodiments, the system uses between 5 to 10 fragment ion spectra for each precursor ion or precursor ion signal. In preferred embodiments, the system uses 5 fragment ion spectra for each precursor ion or precursor ion signal.

In some embodiments, the at most 10 fragment ion spectra are selected for each precursor ion or precursor ion signal based on the precursor retention time. In one embodiment, the at most 10 fragment ion spectra are selected if the fragment ion spectra has a fragment retention time that is similar to the precursor retention time. In one preferred embodiment, 5 fragment ion spectra are selected having five fragment retention times that are closest to the precursor retention time (see FIG. 1B).

Figure 1B:
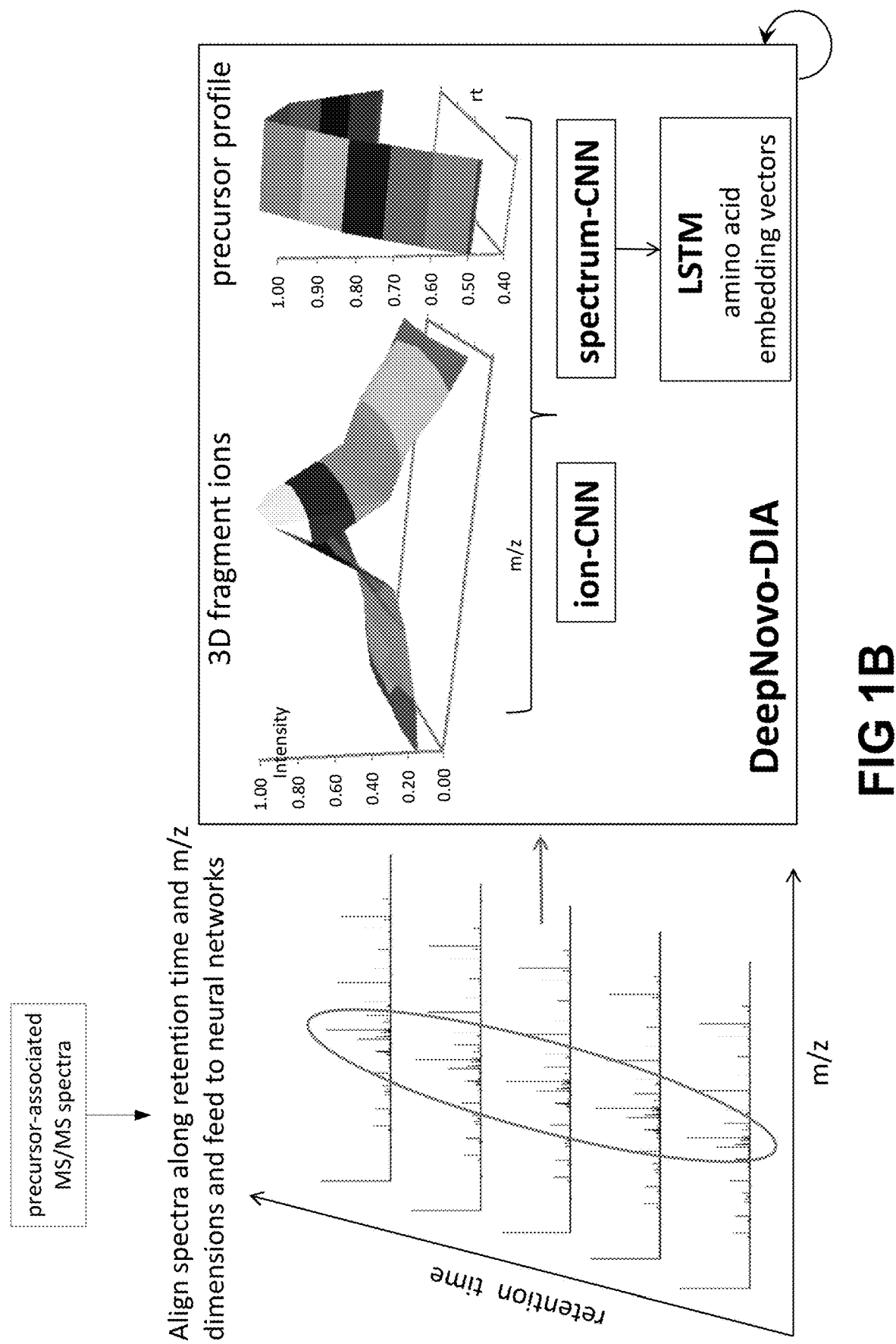

In some embodiments, the fragment ion spectra having fragment retentions times that are the closest to the precursor retention time, are identified by stacking the fragment ion spectra together along fragment retention time dimension, such that the middle or peak fragment ion spectra has a fragment retention time that is closest to the precursor retention time (see FIG. 1B, 3D fragment ions).

Accordingly, mass spectrometry data obtained by DIA comprises one or more of the following variables: precursor ion signals, fragment ion signals, m/z, retention time, and signal intensity.

Mass Spectra Data Format at least one memory, the processor and the at least one memory providing a plurality of layered nodes configured to form an artificial neural network for generating a probability measure for one or more candidates to a next amino acid in an amino acid sequence, the artificial neural network trained on known mass spectrometry spectrum data containing a plurality of known fragment ions peaks of known sequences differing in length and differing by one or more amino acids, wherein the plurality of layered nodes receives a mass spectrometry spectrum data as input, the mass spectrometry spectrum data representing the at least one precursor profile and the fragment ion spectra, and outputs a sequence of the peptide.

In some embodiments, a spectrum is discretized into a vector, called an intensity vector. In some embodiments, the intensity vectors are indexed such that masses correspond to indices and intensities are values. This representation assumes a maximum mass and also depends on a mass resolution parameter. For instance, if the maximum mass is 5,000 Dalton (Da) and the resolution is 0.1 Da, then the vector size is 50,000 and every 1-Dalton mass is represented by 10 bins in the vector. In one embodiment, two types of data are considered: low-resolution (0.1 Da) and high-resolution (0.01 Da). High-resolution data often allow de novo peptide sequencing tools to achieve better accuracy. In some embodiments, the resolution is 0.5 Da, 0.1 Da, 0.05 Da, 0.02 Da, or 0.01 Da.

In some embodiments of the system, the mass spectrometry data or mass spectra are converted into intensity vectors indexed such that mass ranges correspond to indices and intensities are values. For example, the intensity vectors are indexed as follows:

$$\text{Intensity vector} = (I_{(mass=0-0.1Da)}, I_{(mass=0.1-0.2Da)}, I_{(mass=0.2-0.3Da)}, \ldots, I_{(mass=(max-0.1Da)-max)})$$

where "I" is the intensity value as read from the y-axis of mass spectra, for each mass range (or m/z value) taken from the x-axis of the mass spectra. "Da" is the unit, Daltons.

In embodiments of the system involving DIA, the mass spectrometry data or mass spectra are stored as a five dimensional array or matrix. In some embodiments, the mass spectrometry data is stored as a matrix of 5 by 150,000. In some embodiments, the five dimensions are: 1) batch size, 2) number of amino acids, 3) number of ion types, 4) number of associated spectra, 5) window size for identifying fragment ion peaks. In one embodiment, the mass spectrometry data is stores as matrixes or arrays for input to a neural network. In one embodiment, a first matrix or array is used to represent fragment ion spectra. In one embodiment, the first matrix or array is a matrix of the five dimensions listed above. In one embodiment, a second matrix or array is used to represent a precursor profile. The second matrix or array comprises a plurality of dimensions. In one embodiment, the second matrix or array is a matrix of two dimensions comprising batch size and the number of associated spectra. In one embodiment, the second matrix or array is a matrix of the five dimensions listed above. Inputting the first and second matrix or array in parallel is advantageous in that it may speed up the running time of the neural network.

For the batch size dimension, this refers to the number of precursor features that are processed in parallel.

For the dimension associated with the number of amino acids, this refers to the total number of possible amino acids. In one embodiment, there are 20 possible amino acid candidates. In other embodiments, there are 26 possible candidate indications for an amino acid.

For the number of ion types dimension, this refers to, for example, b- and y-ions. In one embodiment, there are 8 types of ions: b, y, b(+2), y(+2), b-H2O, y-H2O, b-NH3, y-NH3; or combinations thereof.

For the number of associated spectra, this refers to the number of fragment ion spectra associated with a precursor profile. In some embodiments, a maximum of 10 fragment ion spectra are used for each precuror profile or ion. In some embodiments, 5 to 10 fragment ion spectra are used for each precuror profile or ion. In one embodiment, 5 fragment ion spectra are used for each precuror profile or ion. It has been found that using more than 10 fragment ion spectra are used for each precuror profile or ion results in little increase in accuracy of the system output, while significantly increasing computational time, load, and cost. It has been found that using at least 5 fragment ion spectra are used for each precuror profile or ion allows for sufficient in accuracy of the system output.

For the window size dimension, this refers to the filter size used in identifying fragment ion peaks. Fragment ion peaks generally adopt a bell-shaped curve, and the systems provided herein are configured to capture or detect the shape of the bell curve by fitting or applying mask filters.

De Novo Sequencing with Neural Networks

In some cases, the challenges facing de novo sequencing can be appreciated as a challenge of automatically generating a description for an image. In one research, a convolutional neural network (CNN), i.e. a type of feed-forward artificial neural network consisting of multiple layers of receptive fields, is used to encode, or to "understand", an image. Then, a long short-term memory (LSTM) recurrent neural network (RNN) is used to decode, or to "describe", the content of the image. That research tries to connect image recognition and natural language processing by integrating two fundamental types of neural networks, CNN and LSTM.

For de novo sequencing, the present systems and methods described herein applies image recognition and description to mass spectrometry data, which requires a different set of parameters and approach compared to known image recognition. For de novo sequencing, exactly one out of $20^L$ amino acid sequences can be considered as the correct prediction (L is the peptide length, 20 is the total number of possible amino acids). Another challenge to de novo sequencing from mass spectrometry data is that peptide fragmentation generates multiple types of ions including a, b, c, x, y, z, internal cleavage and immonium ions [48]. Depending on the fragmentation methods, different types of ions may have quite different intensity values (peak heights), and yet, the ion type information remains unknown from spectrum data.

Furthermore, there are plenty of noise peaks mixing together with the real ions. Finally, the predicted amino acid sequence should have its total mass approximately equal to the given peptide mass. This points to a complicated problem of pattern recognition and global optimization on noisy and incomplete data. In some embodiments, this issue is handled by global dynamic programming [8-10,12,13,15-19,24], divide-and-conquer [11] or integer linear programming [14]. However, there is no naïve application of existing deep learning architectures that work directly on this problem of optimizing de novo sequencing from noisy and incomplete data.

Accordingly, the present inventors have developed systems that allow for deep learning to be applied in de novo peptide sequencing. In some embodiments, adopting neural networks in systems for de novo peptide sequencing allows for greater accuracy of reconstructing peptide sequences. Systems incorporating neural networks also allows for greater coverage in terms of peptides that can be sequenced by de novo peptide sequencing. As well, in some embodiments, access to external databases are not needed.

In one embodiment, a deep learning system is provided for de novo peptide sequencing. The system combines convolutional neural networks (CNNs) and recurrent neural networks (RNNs) to learn features of tandem mass spectra, fragment ions, and sequence patterns of peptides. The networks are further integrated with local dynamic programming to solve the complex optimization task of de novo sequencing. In some embodiments, the system performed better than existing de novo sequencing algorithms by a large margin of 7.7 to 22.9% at the amino acid level and 38.1 to 64.0% at the peptide level. In one embodiment, the system automatically reconstruct the complete sequences of the light and heavy chains of a mouse antibody, achieving 97.5% to 100% coverage and 97.2 to 99.5% accuracy, without using assisting databases. (See for example FIG. 2)

In some embodiments, the system takes advantage of high-performance computing GPUs and massive amount of data to offer a complete end-to-end training and prediction solution. The CNN and LSTM networks of the system can be jointly trained from scratch given a set of annotated spectra obtained from spectral libraries or database search tools. This allows the system to be trained by both general and specific models to adapt to various sources of data. In one embodiment, the system further automatically reconstructs the complete sequences of antibodies, such as the light and heavy chains of an antibody. Determining the sequences of antibodies, including novel antibodies, is one application of peptide sequencing and the present systems and methods. Antibody sequencing previously required de novo sequencing, database search, and homology search together to succeed [21]. An example of antibody sequencing systems and methods are disclosed in U.S. patent application Ser. No. 15/599,431, the entire content of which is hereby incorporated by reference. The present systems and methods do not require a database search or homology search.

Moreover, the system is re-trainable to adapt to various sources of data and in some embodiments provides a complete end-to-end training and prediction solution to the de novo sequencing problem.

In some embodiments, the system solves optimization problems by utilizing deep learning and dynamic programming. In some embodiments, the system comprises a processor, such as a central processing unit (CPU) or graphics processing unit (GPU). Preferably, the system comprises a GPU.

Neural Network

In some embodiments, a processor and at least one memory provides a plurality of layered nodes to form an artificial neural network. The process is configured to determine the amino acid sequence of a peptide.

In some embodiments, the system comprises a neural network. The system receives a sequence that has been predicted up to the current iteration or position in the peptide sequence and outputs a probability measure for each of the next possible element in the sequence by interpreting the fragment ion peaks of the mass spectra. In one embodiment, the system iterates the process until the entire sequence of the peptide is determined.

In one embodiment, the neural network is a convolutional neural network (CNN). In another embodiment, the neural network is a recurrent neural network (RNN), preferably a long short-term memory (LSTM) network. In yet another embodiment, the system comprises a CNN and a RNN arranged in series, for first encoding the intensity vectors from mass spectra into feature vectors and then predict the next element in the sequence in a manner similar to predictive text (for predicting the next word in a sentence based on the context of other words and the first letter typed). In one preferred embodiment, the system comprises both a CNN and a RNN arranged in parallel. In some embodiments, the system comprises one or more CNNs and one or more RNNs.

As used herein, a "prefix" refers to a sequence of amino acids that have been predicted up to the current iteration. In some embodiments, a prefix includes a "start" symbol. In one preferred embodiment, a fully sequenced peptide sequence begins with the "start" symbol and ends with an "end" symbol. The prefix is indexed, for example, using the single-letter representation of amino acids or the amino acid name.

For example, a prefix is indexed as:

prefix={start,P,E,P} and the mass of this prefix ("prefix mass") is indexed as:

prefix_mass=mass[N-term]+mass[P]+mass[E]+mass[P]

CNN

In embodiments of the system comprising a CNN, the CNN comprises a plurality of layers. In some embodiments, the CNN comprises at least one convolutional layer and at least one fully connected layer. In some embodiments, the CNN comprises one convolutional layer and two fully connected layers. In other embodiments, the CNN comprises two convolutional layers and one fully connected layer. In preferred embodiments, the CNN comprises 2 convolutional layers and 2 fully connected layers. In other embodiments, the CNN comprises a different combination and/or quantity of convolutional layer(s) and connected layer(s). A convolutional layer applies a convolution operation to the input, passing the result to the next layer; while fully connected layers connect every neuron in one layer to every neuron in another layer.

The inventors have found that adding a second convolutional layer to the first convolutional layer, as well as adding a second fully connected layer to the first connected layer, both significantly increased the accuracy of the system. Adding further convolutional layers or fully connected layers beyond the first two in both cases may yield greater accuracy but these increases in accuracy were not significant. Instead, having more than two convolutional layers or two fully connected layers increased the computational and processing burden of the system, thereby increasing the demand for processing power needed for the system to operate.

In some embodiments, the first convolution layer is configured to detect the fragment ion peaks of a mass spectrum by image processing, wherein the mass spectra data is stored as, for example, intensity vectors as described above. As used herein, in image processing, a kernel, convolution matrix, or mask is a small matrix, which is used for blurring, sharpening, embossing, edge detection, and more. For example, this is accomplished by performing a convolution between a kernel and an image (such as a mass spectra), which is the process of adding each element of the image to its local neighbors, weighted by the kernel. The fragment intensity peaks of a mass spectrum can be characterized as a bell curve, and the first convolutional layer is configured to capture or detect the shape of the bell curve by fitting or applying mask filters sized according to the kernel used.

In some embodiments, the system further comprises a Rectified Linear Unit (ReLU) to add nonlinearity to the neural network. The ReLU is configured to capture the curvature of the bell curve.

In further embodiments, the system further applies dropout to a layer. As used herein "dropout" is a regularization technique for reducing overfitting in neural networks by preventing complex co-adaptations on training data. To apply dropout, neuron units are randomly activated (or dropped) at every training iteration so that they do not co-adapt. In one embodiment, the dropout probability for a convolutional layer is 0%-25%, preferably 25%. In another embodiment, the dropout probability for a fully connected layer is 0%-50%, preferably 50%.

In some embodiments, ReLU is applied to each convolutional and/or fully connected layer. In other embodiments, dropout is applied to each convolutional and/or fully connected layer. In preferred embodiments, ReLU and dropout are applied to each convolutional and/or fully connected layer.

In preferred embodiments, a second convolutional layer is applied on top of the first convolutional layer. The second convolution layer is similar in configuration to the first convolutional layer, and is configured to apply a second fitting of filters on top of the first. The second convolutional layer differs from the first in that it uses a finer filter with a smaller window size to more finely capture the bell curve shape of the fragment ion peaks of a mass spectrum.

The convolutional layers are followed by fully-connected layers (also known as hidden layers). In some embodiments, where the CNN comprises two fully-connected layers, the first fully-connected layer comprises 128-2000 neuron units. In one embodiment, the first fully-connected layer comprises 128-250 neuron units or 1000-2000 neuron units. In preferred embodiments, the first fully-connected layer comprises 512 neuron units, to maximize accuracy of the system while at the same time minimizing the processing power needed by the system.

Given a prefix input, the CNN is used for detecting particular fragment ions in the mass spectrum. In one embodiment, a fully-connected layer is configured to fit known fragment ions to the mass spectrum. In one preferred embodiment, the first fully-connected layer is configured to identify the next possible amino acid by fitting the corresponding b- and y-ions to the mass spectrum image. In another preferred embodiment, by fitting b- and y-ions corresponding to the next amino acid to be determined in a peptide sequence. For example, given a 10 amino acid long peptide and a prefix input comprising the first 3 amino acids from the amino end of the peptide that has already been determined, the system iteratively goes through each of the 20 possible amino acids to identify candidate 4th amino acid for this peptide. Using the example of Alanine as the 4th amino acid, the mass of the prefix and the 4th amino acid Alanine is determined. Since a mass spectrum involves the fragmentation of peptides, for a 4 amino acid long fragment from the amino end of the peptide, there is a corresponding 6 amino acid long fragment from the C-end of the peptide, using this example. These two fragments are called b-ions and y-ions. The first fully-connected layer is configured to take these b-ions and y-ions for each candidate next amino acid in the sequence and fits the b-ions and y-ions against the mass spectrum. Matches with fragment peaks in the mass spectrum means that these b-ions and y-ions are present in the fragments generated by the mass spectrum, and in turn more likely that the candidate amino acid is the next one in the sequence.

In some embodiments, the CNN is trained on one or more mass spectra of one or more known peptides. In other embodiments, the CNN is trained on one or more mass spectra with ion peaks corresponding to known peptide fragments. These known peptide fragments have varying lengths and sequences. In some embodiments, these known peptide fragments vary by one amino acid residue in length. In one embodiments, for each set of known peptide fragments of the same length, they each vary by one amino acid at a particular location. In yet other embodiments, these known peptide fragments are pairs of b-ions and y-ions.

In some embodiments, the last fully-connected layer has as many neuron units as the number different possible elements for a sequence. For example, the last fully-connected layer may have at least 20 neuron units, based on the 20 possible amino acids. In one embodiment, the last fully-connected layer has 26 neuron units corresponding to 26 possible symbols or elements to predict from. The 26 symbols refers to "start", "end", "padding", the 20 possible amino acids, three amino acid modifications (for example: carbamidomethylation (C), Oxidation (M), and Deamidation (NQ)) for a total of 26. The "padding" symbol refers to blanks.

The output from the final fully-connected layer is a probability measure for each of the next possible element in the sequence. This output is stored as, for example, data tables, vectors, data arrays, or data strings comprising pairs of candidate amino acid and the corresponding probability, where values can be stored in corresponding data fields and data instances. For example, given an input prefix comprising the first three predicted amino acids, the output for the 4th candidate amino acid is indexes as a probability vector: [(Alanine, 80%), (Arginine, 15%), (Asparagine, 5%)]. In some embodiments, the output is a probability distribution, summing up to a total of 100%.

In some embodiments, a filter or set of filters (for example, in the first convolutional layer) are applied to image data or processed image data (for example, a data representation of a mass spectra image or portion of same such as a peak) to identify features that the CNN has been trained to recognize as corresponding to a b-ion or y-ion containing a particular amino acid at a particular location in an original peptide sequence. In these embodiments, the CNN is configured to use an additional filter or sets of filters to identify features that the CNN has been trained to recognize as corresponding to a b-ion or y-ion containing a particular amino acid at a particular location of the original peptide sequence, for each of the other possible amino acids at each of the other possible locations in the original peptide sequence. In some embodiments, the fully connected layer of the CNN outputs a probability vector that the original mass spectrometry image, portion thereof, or data representation of same contains each of the possible amino acids at the specific sequence location. The CNN can then be used to generate a probability vector of the original mass spectrometry image, portion thereof, or data representation of same for each of the other sequence locations. In this way, in some embodiments, the CNN is used to predict the amino acid sequence of a peptide based on mass spectrometry data of b-ions and y-ions or other peptide fragments.

In preferred embodiments, the final output of the system is a vector of 26 signals, or logits vector (unscaled log probabilities), corresponding to the probability of each of the 26 possible symbols being the next element in the sequence. To identify the next amino acid in a peptide sequence, the amino acid or symbol with the highest probability is chosen.

RNN

In one embodiment comprising a RNN, the system comprises a spectrum-CNN connected to a RNN. The RNN is preferably a LSTM, In one embodiment, the spectrum-CNN or the system is configured to encode the intensity vectors from mass spectra into "feature vectors", before the features vectors are inputted into a LSTM network. In some embodiments, the spectrum-CNN determines the present of individual amino acids present in a peptide by identifying fragment ion peaks corresponding to individual amino acids. In one embodiment, the spectrum-CNN determines the presence of individual amino acids or short segments of amino acid sequences by identifying corresponding fragment ion peaks. In preferred embodiments, the spectrum-CNN determines the present of individual amino acids present in a peptide by identifying fragment ion peaks that differ by one amino acid and calculating the mass difference between the two fragment ion peaks.

In some embodiments, the spectrum-CNN comprises one or more convolutional layers, preferably two layers, and one or more fully-connected layers. In some embodiments, the spectrum-CNN is configured in the same manner as the CNN embodiments described above, except to the extent of predicting the next amino acid in the sequence. In preferred embodiments, the system is configured to first slice each input intensity vector into pieces based on the amino acid masses. For example, the mass of Alanine, or "A", is 71.0 Da and if the intensity vector has mass ranges of 0.1 Da, the intensity vector is sliced by every index of 710 until the end, converting the intensity vector into a feature vector indexed for example as:

$$\text{Feature vector} = (I_{(mass=0-aa)}, I_{(mass=aax1-aax2)}, I_{(mass=aax2-aax3)}, \ldots)$$

where "aa" refers to amino acid. This procedure is repeated for each possible symbol or element. For example, in the case of 20 amino acids, each intensity vector is sliced into 20 feature vectors. The sliced vectors are inputted through the spectrum-CNN, and outputted as a vector of a size corresponding to the number of neuron units of the last fully-connected layer. In one embodiment, the spectrum-CNN comprises one fully-connected layer of, for example, 512 neuron units and therefore outputs a vector of size 512.

The output from the spectrum-CNN is input into a LSTM. In some embodiments, the output from the spectrum-CNN is a vector or array listing the amino acids present in a peptide. In one embodiment, the output from the spectrum-CNN is a vector or array listing the amino acid identity and number of said amino acid in a peptide.

The architectural configuration of a LSTM is known to a skilled person, for example as described in reference [34], the entire content of which is incorporated herein by reference. In some embodiments, the LSTM comprises at least one layer. In preferred embodiments, the LSTM comprises 2 or 3 layers, preferably 3 layers for DIA data. In other embodiments, each layer comprises 128-2000 neuron units, preferably, 512 neuron units. The LSTM is configured to embed the inputted vectors (such as the vector of size 512) to represent each of the, for example, 26 symbols into a 2-dimensional array. The system iteratively inputs the vector of size 512 through the LSTM, with the first iteration of vector of size 512 being the output from the spectrum-CNN, and outputs a predicted candidate next amino acid in the sequence.

In other embodiments, the LSTM is configured to embed the inputted vectors according to the systems and procedures described in U.S. patent application Ser. No. 15/599,431, publication no. US20170336419A1, titled METHODS AND SYSTEMS FOR ASSEMBLY OF PROTEIN SEQUENCES, the entire content of which is incorporated herein by reference.

In some embodiments, the LSTM further comprises a last fully-connected layer of 26 neuron units, or as many neuron units as there are possible elements at a given position in a sequence, to perform a linear transformation of the vector of 512 output into signals of 26 symbols to predict. In one embodiment, the output from the last fully-connected layer is a probability measure for each of the possible 26 symbols.

CNN and RNN

In some embodiments where the system comprises both a CNN and a RNN in parallel, the system first concatenates or links the outputs of each respective second-to-last layers (for example, second last fully-connected layer of the CNN and the second last layer of the LSTM). Using the above examples, where the second last fully-connected layer of the CNN has 512 neuron unit yielding a vector of size 512, and the second last layer of the LSTM also yields a vector of size 512, these two vectors are combined into a vector of size 1024. In one embodiment, the system further adds on a fully-connected layer having a number of neuron units corresponding to the size of the combined vector (for example, combined vector of size 1024 above). In preferred embodiments, the system further applies ReLU activation and dropout as described above. Lastly, the system further adds another fully-connected layer of as many neuron units as there are possible elements at a given position in a sequence (for example, 26 neuron units), to yield an output of probability measures of each of the candidate next amino acid.

In preferred embodiments, the final output of the system is a vector of 26 signals, or logits vector (unscaled log probabilities), corresponding to the probability of each of the 26 possible symbols being the next element in the sequence. To identify the next amino acid in a peptide sequence, the amino acid or symbol with the highest probability is chosen.

DIA Ion-CNN Model

Figure 4:
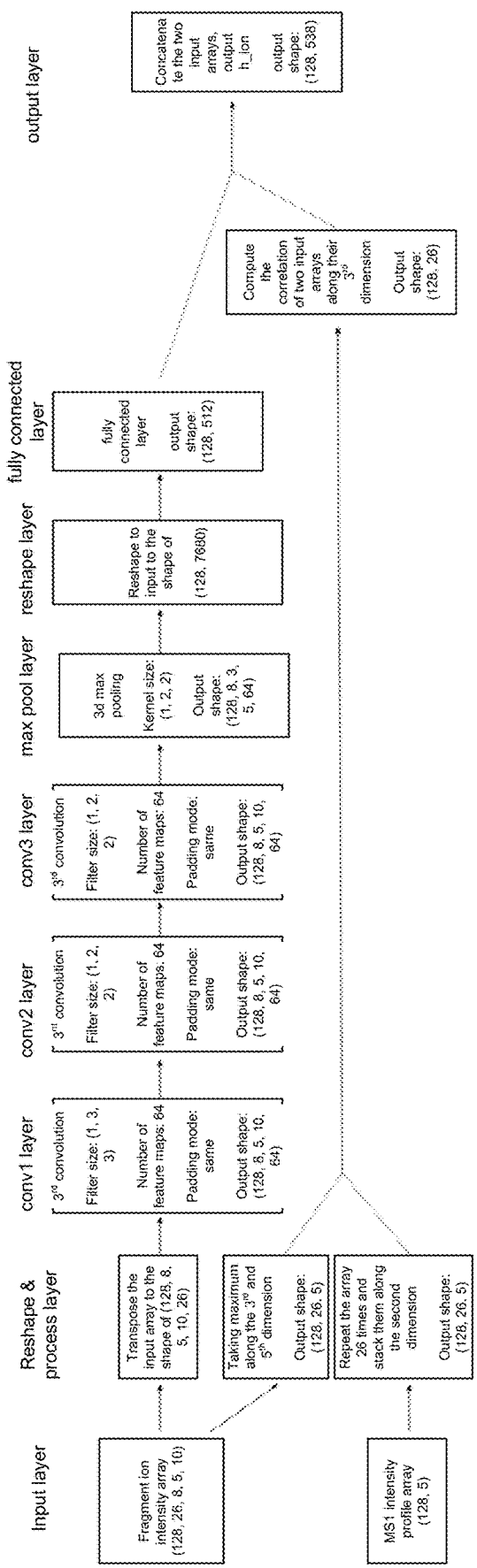
FIG. 4 shows a schematic diagram showing an ion-CNN model.

Turning to FIG. 4, an embodiment of ion-CNN for DIA is illustrated. In some embodiments of an ion-CNN for DIA, the system inputs two sets of inputs. In one embodiment, the first matrix or array described herein comprises the first input, and the second matrix or array described herein comprises the second input.

In some embodiments, the system inputs the first matrix or array into a plurality of convolutional layers. In some embodiments, there are two or more convolutional layers. In other embodiments, there are three or more convolutional layers. In one embodiment, there are three convolutional layer. In some embodiments, an ion-CNN for DIA has more convolutional layers than DDA data. In some embodiments, the first matrix or array is inputted into a single final fully connected layer. In some embodiments, the first matrix or array is inputted through three convolutional layers followed by one max pooling layer and one fully-connected layer.

In some embodiments, the system inputs the second matrix or array in parallel with the first matrix or array.

DIA Spectrum-CNN Model

Figure 6:
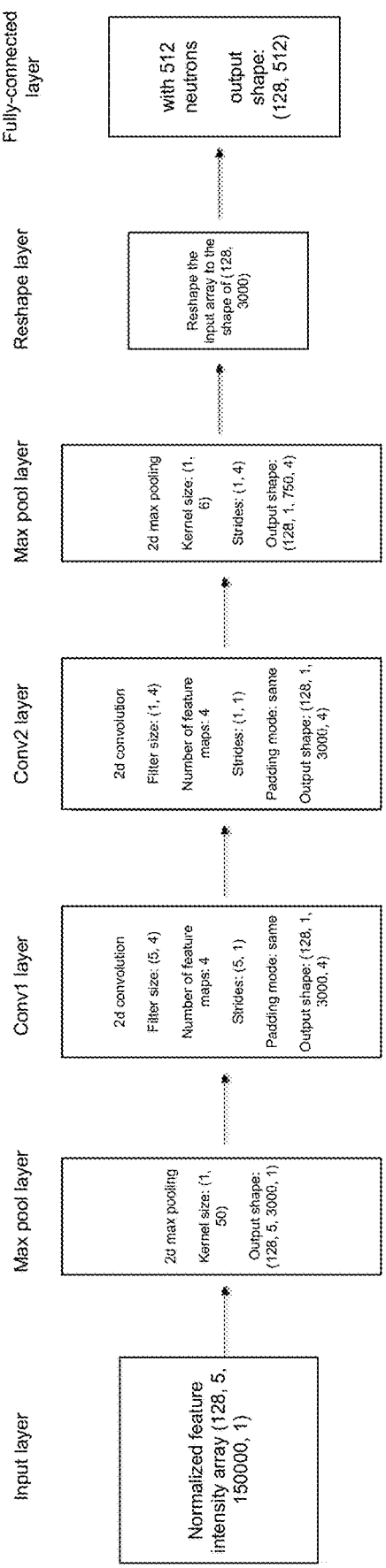
FIG. 6 shows a schematic diagram showing an Spectrum-CNN model.

Turning to FIG. 6, some embodiments of the system comprises a long short-term memory (LSTM) network for DIA. In some embodiments of the LSTM for DIA, the neural network has one or more convolutional layers. In one embodiment, there are two convolutional layers. In one embodiment, the LSTM has one final fully connected layer. In one embodiment, the LSTM has one max pooling layer, two convolution layers and one fully connected layer.

Other Embodiments

In one preferred embodiment, while selecting the next amino acid, the system is configured to calculate the suffix mass and employs knapsack dynamic programming to filter out those amino acids whose masses do not fit the suffix mass. As used herein, "suffix mass" refers to the sum total mass of the amino acids remaining to be predicted. The prefix mass and the suffix mass must add up to equal the total mass of the peptide that is being sequenced. In embodiments where knapsack is applied to filter out amino acids whose masses do not fit the suffix mass; the recall and/or accuracy of the system were increased.

In preferred embodiments, the system performs bi-directional sequencing and uses two separate sets of parameters, forward (for example, sequencing from the amino end of the peptide) and backward (for example, sequencing from the carboxylic end of the peptide), for the CNN. This is not done for the spectrum-CNN and the embedding vectors. The present inventors have found that embodiments of the system that perform bi-directional sequencing achieves better accuracy than using only one direction.

In most preferred embodiments, the system is configured to predict the next amino acids using a beam search to optimize the prediction. As used herein "beam search" refers to a heuristic search where instead of predicting the next element in a sequence one at a time at each iteration based on probability, the next n-elements are predicted based on the overall probability of the n-elements. For example, where n=5, the system predicts the next 5 amino acids at a time in the sequence at each iteration based on the an overall probably of the next 5 candidate amino acids sequences which is derived from the product of each individual amino acid probabilities.

In some embodiments, there is provided a computer implemented system for de novo sequencing of peptides from mass spectrometry data using neural networks, the system including one or more processors and non-transitory computer readable media, the computer implemented system comprising: a mass spectrometer configured to generate a mass spectrometry spectrum data of a peptide (or, in some embodiments, a portion of a peptide or a biological sequence or portion thereof); a processor configured to: generate an input prefix representing a determined amino acid sequence of the peptide. In some embodiments, the determined amino acid sequence of the peptide can include a sequence of one or more amino acids. In some embodiments, the determined amino acid sequence of the peptide can include a "start" symbol and one or more or zero amino acids that have been predicted up to the current iteration. The processor, in these embodiments, is further configured to iteratively update the determined amino acid sequence with a next amino acid. In these embodiments, the computer implemented system comprises a neural network configured to iteratively generate a probability measure for one or more candidate fragment ions (e.g., a candidate fragment ion can be a fragment ion having a particular amino acid at a particular location in the sequence as compared to a separate candidate fragment ion that has a different particular amino acid at that same particular location in the sequence). In some embodiments, there may be a candidate fragment ion each corresponding to each of 20 amino acid residues, their modifications, and special symbols. The iterative generation of a probability measure may be based on one or more fragment ion peaks of the mass spectrometry spectrum data and the corresponding masses of the fragment ion peaks, to determine the next amino acid, wherein the neural network is trained on a known mass spectrometry spectrum data. In some embodiments, the neural network comprises: at least one convolutional layer configured to apply one or more filters to an image data representing the mass spectrometry spectrum data to detect fragment ion peaks; and at least one fully-connected layer configured to determine the presence of a fragment ion peak corresponding to the next amino acid and output the probability measure for each candidate fragment ion.

In some embodiments, the processor is configured to convert the mass spectrometry spectrum data into an intensity vector listing an intensity value for each mass range, and the at least one convolutional layer is configured to apply one or more filters to an image data of the intensity vector. In some embodiments, the intensity value can be a sum of intensity values corresponding to one or more or all fragment ions having a mass in the corresponding range.

In some embodiments, an intensity vector can include or list intensity values for mass ranges or masses. For example, an intensity value can be a sum of one or more intensity values or can be a net intensity value.

In some embodiments, there is provided a computer implemented system for de novo sequencing of peptides from mass spectrometry data using neural networks, the system including one or more processors and non-transitory computer readable media, the computer implemented system comprising a mass spectrometer configured to generate a mass spectrometry spectrum data of a peptide; a processor configured to: convert the mass spectrometry spectrum data into an intensity vector listing intensity values for mass ranges over the mass spectrometry spectrum data, generate an input prefix representing an determined amino acid sequence of the peptide, and iteratively update the determined amino acid sequence with a next amino acid. In these embodiments, the computer implemented system further comprises a neural network configured to iteratively identify the best possible candidate for the next amino acid, wherein the neural network comprises: a convolutional neural network (CNN) configured to generate one or more output vectors representing one or more amino acids represented in the spectrum, using one or more intensity vectors corresponding to image data; and a recurrent neural network (RNN) trained on a database of known peptide sequences, and configured to predict the next amino acid by vector embedding using one or more of the one or more output vectors.

In some embodiments, there is provided a computer implemented system for de novo sequencing of peptides from mass spectrometry data using neural networks, the system including one or more processors and non-transitory computer readable media, the computer implemented system comprising: a mass spectrometer configured to generate a mass spectrometry spectrum data of a peptide; a processor configured to: convert the mass spectrometry spectrum data into an intensity vector listing intensity values for mass ranges over the mass spectrometry spectrum data, generate an input prefix representing an determined amino acid sequence of the peptide, and iteratively update the determined amino acid sequence with a next amino acid. In these embodiments, the computer implemented system further comprises a first neural network configured to iteratively generate a probability measure for all possible candidate fragment ions based on fragment ion peaks of the mass spectrometry spectrum data and the corresponding masses of the fragment ion peaks, to determine the next amino acid, wherein the neural network is trained on a known mass spectrometry spectrum data, and wherein the first neural network comprises: at least one convolutional layer configured to apply one or more filters to an image data representing the mass spectrometry spectrum data to detect fragment ion peaks; and and at least one fully-connected layer configured to determine the presence of a fragment ion peak corresponding to the next amino acid. In these embodiments, the computer implemented system further comprises a second neural network configured to iteratively identify the best possible candidate for the next amino acid, wherein the second neural network comprises: a spectrum-convolutional neural network (spectrum-CNN) configured to encode the mass spectrometry fragment ion data into a feature vector; and a recurrent neural network (RNN) configured to predict a next amino acid in a peptide sequence; wherein the first and second neural networks share at least one common last fully-connected layer configured to output the probability measure for each possible entry for the next amino acid.

Sequence Output

In some embodiments, the processors and/or the system is configured to generate signals for outputting at least a portion of the determined sequence. In some embodiments, the output can represent at least a partially determined sequence. In some embodiments, the output can represent one or more partially determined sequences. In some instances, the one or more partial determined sequences can be combined into a fully determined sequence. In some embodiments, the output can include a fully determined sequence or a portion of the fully determined sequence.

In some embodiments, generating signals for outputting at least a portion of a determined sequence can include generating signals for display the output on a visual display or screen, generating signals for printing or generating a physical representation of the output, generating signals for providing an audio representation of the output, sending a message or communication including the output, storing the output in a data storage device, generating signals for any other output and/or any combination thereof.

In some instances, the determined sequence outputted by the systems provided herein is used for novel protein discovery, for example, for antibody characterization. In some embodiments, the determined sequences outputted by the systems provided herein is used for generating antibodies for diagnostic kits or diagnostic imaging. In some embodiments, the determined sequences outputted by the systems provided herein is used for generating antibodies for new disease therapies. In some embodiments, the determined sequences outputted by the systems provided herein is used for generating antibodies for prenatal therapy. In some embodiments, the determined sequences outputted by the systems provided herein is used for vaccine development. In some embodiments, the determined sequences outputted by the systems provided herein is used for developing immunoassays.

Computing Device

Figure 15:
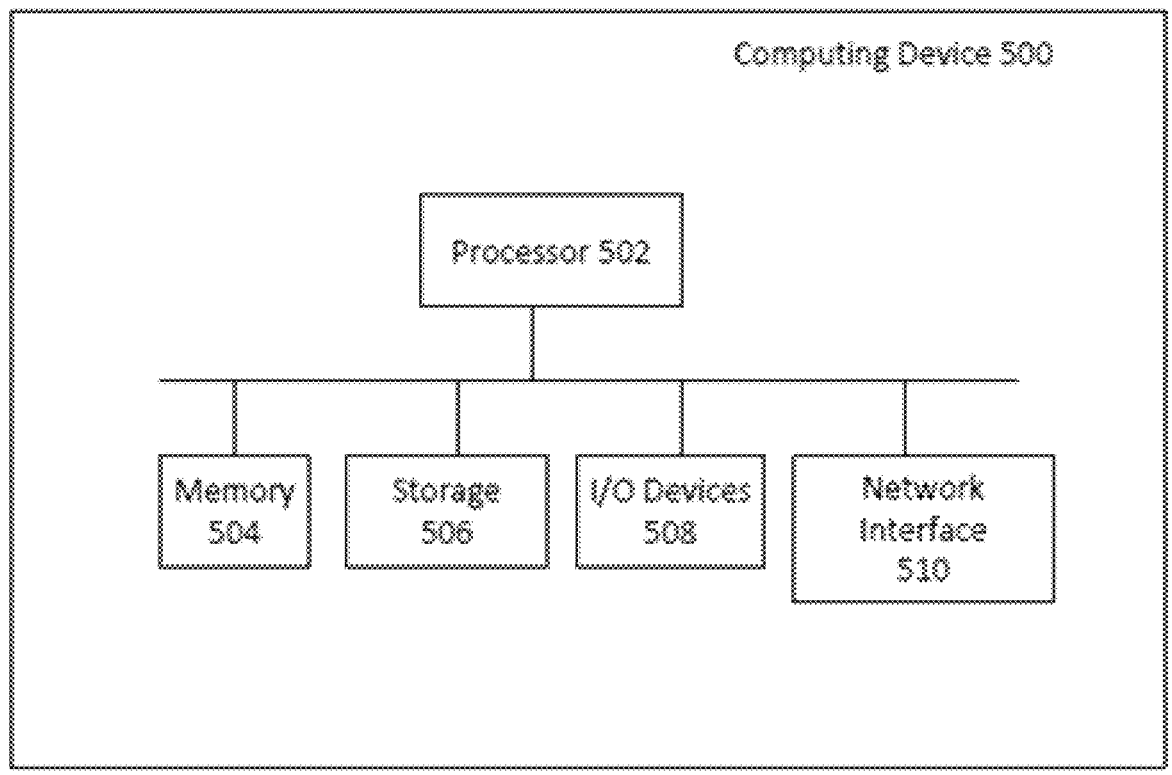
FIG. 15 is a block diagram of an example computing system configured to perform one or more of the aspects described herein.

FIG. 15 is a block diagram of an example computing device 500 configured to perform one or more of the aspects described herein. Computing device 500 may include one or more processors 502, memory 504, storage 506, I/O devices 508, and network interface 510, and combinations thereof. Computing device 500 may be a client device, a server, a supercomputer, or the like.

Processor 502 may be any suitable type of processor, such as a processor implementing an ARM or x86 instruction set. In some embodiments, processor 502 is a graphics processing unit (GPU). Memory 504 is any suitable type of random access memory accessible by processor 502. Storage 506 may be, for example, one or more modules of memory, hard drives, or other persistent computer storage devices.

I/O devices 508 include, for example, user interface devices such as a screen including capacity or other touch-sensitive screens capable of displaying rendered images as output and receiving input in the form of touches. In some embodiments, I/O devices 508 additionally or alternatively include one or more of speakers, microphones, sensors such as accelerometers and global positioning system (GPS) receivers, keypads, or the like. In some embodiments, I/O devices 508 include ports for connecting computing device 500 to other computing devices. In an example embodiment, I/O devices 508 include a universal serial bus (USB) controller for connection to peripherals or to host computing devices.

Network interface 510 is capable of connecting computing device 500 to one or more communication networks. In some embodiments, network interface 510 includes one or more or wired interfaces (e.g. wired ethernet) and wireless radios, such as WiFi, Bluetooth, or cellular (e.g. GPRS, GSM, EDGE, CDMA, LTE, or the like). Network interface 510 can also be used to establish virtual network interfaces, such as a Virtual Private Network (VPN).

Computing device 500 operates under control of software programs. Computer-readable instructions are stored in storage 506, and executed by processor 502 in memory 504. Software executing on computing device 500 may include, for example, an operating system.

The systems and methods described herein may be implemented using computing device 500, or a plurality of computing devices 500. Such a plurality may be configured as a network. In some embodiments, processing tasks may be distributed among more than one computing device 500.

While particular embodiments of the present invention have been illustrated and described, it would be obvious to those skilled in the art that various other changes and modifications can be made. The claims should therefore not be limited by the above described embodiment, systems, methods, and examples, but should be given the broadest interpretation within the scope and spirit of the invention as claimed.

EXAMPLES

DeepNovo

In U.S. patent application Ser. No. 16/037,949, the entire content of which is incorporated herein by reference, a deep learning-based model for de novo sequencing of DDA data was provided. Using neural networks to better learn the features of fragment ions and peptide sequences, lead to improvements in sequencing accuracy. In contrast to existing complicated optimization systems, the iterative sequencing framework of DeepNovo allows for extension to DIA data little increase in complexity. To interpret highly multiplexed spectra, the neural networks were reconstructed to utilize the extra dimensionality of DIA data (m/z and retention time) to identify co-eluting patterns of a precursor ion and its fragment ions, as well as fragment ions across multiple neighbor spectra. This additional data allows DeepNovo to identify the correct signal for de novo sequencing amid a large amount of noise in a DIA spectrum.

Given the presence of multiple peptides in the same spectrum, de novo sequencing as identified as a multi-label classification problem with dense signals, and a focal loss [12] was identified and applied as the suitable objective function for DIA data. The focal loss down-weights the contribution of easy predictions and puts more focus on hard predictions, and therefore, facilitates in addressing the problems of noisy targets and class imbalance.

One embodiment of the system, called DeepNovo is illustrated in FIGS. 1A and 1B. First, precursor ion features are detected together with their m/z, charge, retention time and intensity profile from the LC-MS map [13]. Next, for each precursor feature, all MS/MS spectra were collected so that they are within the precursor's retention time range and their DIA m/z windows must cover the precursor's m/z. As the number of spectra collected for a precursor may vary, a fixed number of spectra was selected that are closest to the center of the precursor's retention time. The closer a spectrum is to the center of the precursor's retention time, the stronger are its fragment ion signals for de novo sequencing. The correlation between the precursor's intensity profile and its fragment ions is a good indicator for de novo sequencing. Hence, the precursor and its associated MS/MS spectra were fed into DeepNovo neural networks to learn (i) the 3D shapes along m/z and retention time dimensions of fragment ions, (ii) the correlation between the precursor and its fragment ions, and (iii) the peptide sequence patterns. The DeepNovo de novo sequencing framework operates in a recurrent and beam-search fashion: at each iteration, the model predicts the next amino acid by conditioning on the output of previous steps and only keeps track of a constant number of top candidate sequences. As a result, its complexity does not increase with the number of peptides nor the number of ions in the spectrum.

Data Preprocessing

As a DIA spectrum is highly multiplexed, it is preferred to use high resolution to distinguish fragment ions from different precursors that accidentally have similar masses. In this study, 50 bins were used to represent 1.0 Dalton (Da), i.e. a resolution of 0.02 Da. A maximum mass value of 3,000.0 Da was defined. Thus, each spectrum was represented by a vector of size 150,000, in which the mass of an ion corresponds to an index and the ion intensity is the vector value at that index. As for the retention time dimension, this number was fixed and selected those spectra closest to the feature's retention time mean. If there were not enough spectra, zeros were appended. In one study, 5 spectra was used (using 10 spectra showed minor improvements). The spectra were stacked together along the retention time dimension so that the middle one was the closest to the feature's retention time mean (FIGS. 1A and 1B).

The MS/MS spectra information of a feature is stored in a matrix of size 5 by 150,000. To normalize the intensities, the feature matrix was element-wise divided by its maximum. In the meantime, to make use of MS1 information, the MS1 intensity profiles of the selected 5 spectra was also extracted. The resulting normalized 5 by 150,000 matrix together with the length-5 MS1 intensity profile vector are then fed to the DeepNovo model for de novo sequencing.

De Novo Sequencing Framework

Figure 2:
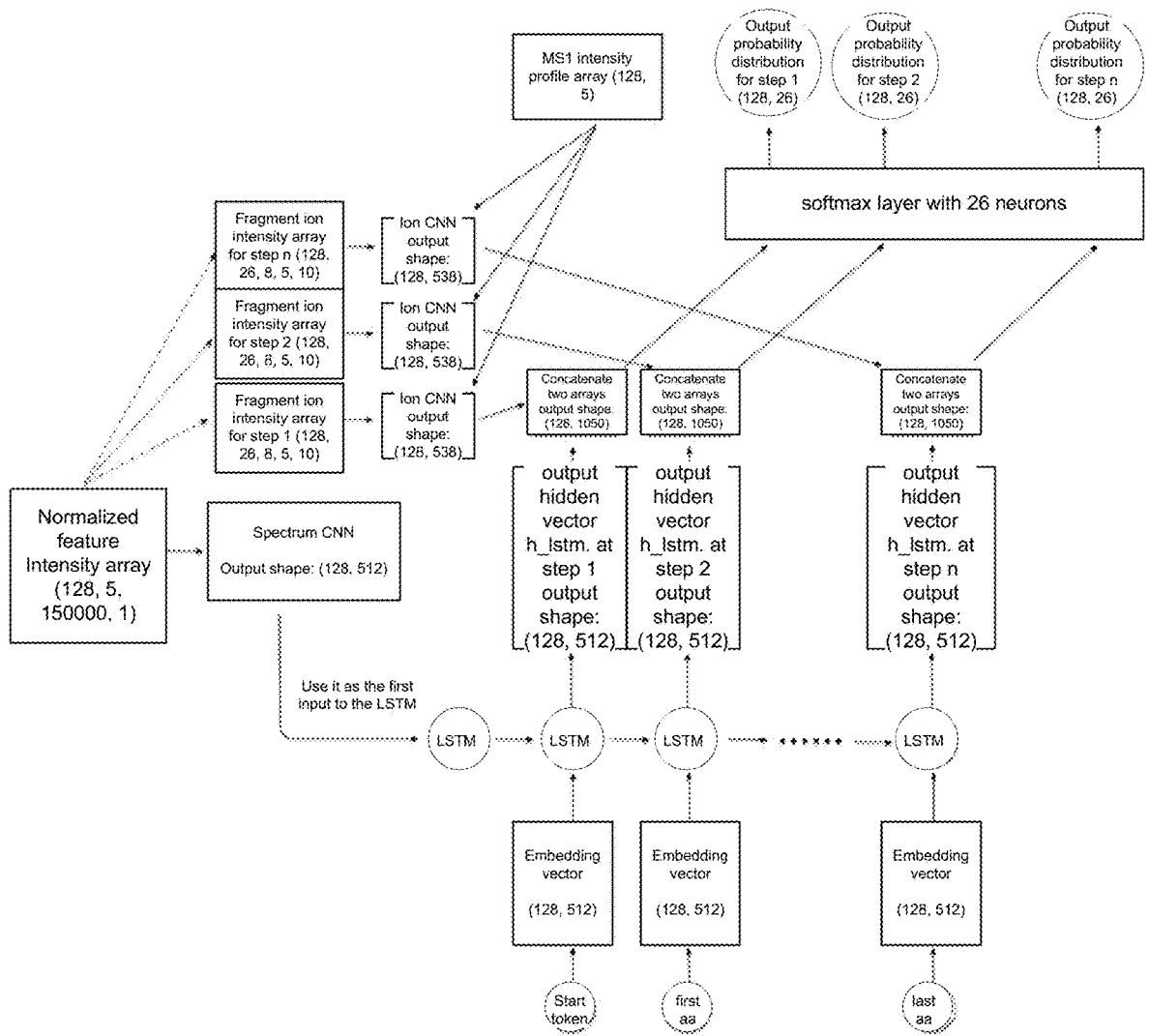
FIG. 2 is a schematic diagram showing a DeepNovo sequencing framework.

The de novo sequencing framework is similar for DDA and DIA data. However for DIA data, extra pre-processing is needed to add the retention time dimension of DIA data. The framework is illustrated in FIG. 2. The framework operates in a recurrent and beam-search fashion: at each iteration, the model predicts the next amino acid by conditioning on the output of previous steps and only keeps track of top 5 candidate sequences. For each iteration, the input is a prefix, i.e., a sequence including a "start" symbol and the amino acids that have been predicted up to the current iteration. The output is a probability distribution over 26 candidates, including 20 amino acid residues, their modifications (oxidation (M) and deamidations (NQ)), and three special symbols "start", "end", 62 and "padding".

Ion-CNN

In some embodiments, the ion-CNN is configured to learn features (the peaks) of fragment ions in a spectrum and summarizes the overall information. The input data to the ion-CNN is a prefix, i.e., a sequence including the "start" symbol and the amino acids that have been predicted up to the current iteration. The output is a probability distribution over 20 amino acid residues, their modifications, and three special symbols "start", "end", and "padding". In one embodiment, three modifications are considered: fixed modification carbamidomethylation (C), and variable modifications Oxidation (M) and Deamidation (NQ), hence, a total of 26 symbols are used for prediction. For example, where the fourth amino acid is considered, the prefix consists of four symbols "start", "P", "E", "P". Symbol "T" is predicted as the next amino acid ($4^{th}$ amino acid in this example) by sampling or by selecting the highest probability from the model output probability distribution.

Given the input prefix (prefix={start, P, E, P}), in one embodiment, DeepNovo first computes the prefix mass (prefix_mass=mass[N-term]+mass[P]+mass[E]+mass[P]), i.e., the sum of masses of N-terminal and amino acids in the prefix. Next, DeepNovo tries to add each of 26 symbols to the current prefix and updates its mass accordingly. For each candidate, the corresponding masses of b-ions and y-ions are calculated. In the current implementation, 8 ion types are used: b, y, b(2+), y(2+), b-$H_2O$, y-$H_2O$, b-$NH_3$, and y-$NH_3$ Given an ion mass, DeepNovo identifies its location on the intensity vector using the mass resolution. For example, the prefix of four symbols "start", "P", "E", "P" with the next candidate "T" will have a b-ion of mass 424.2 Da, which corresponds to index 4240 on the intensity vector of resolution 0.1 Da. DeepNovo then extracts an intensity window of size 10 around the ion location. Thus, for each input prefix, DeepNovo computes a 3-dimensional array of shape 26×8×10. Deep learning libraries often process data in batches to take advantage of parallel-computing. Here a batch size of 128 is used, i.e., 128 prefixes were processed at the same time and their arrays are packed into a 4-dimensional array of shape 128×26×8×10. The shape was further transposed into 128×26×8×10 (explained in further detail below). This final array, denoted by $X^{128 \times 26 \times 8 \times 10}$, is similar to the common data setting of image processing where the $1^{st}$ dimension is the number of images, the $2^{nd}$ is the height, the $3^{rd}$ is the width, and the $4^{th}$ is the number of channels (e.g., 3 for Red-Green-Blue or 1 for Black-White).

In some embodiments, the ion-CNN model is a convolutional neural network with two convolutional layers and two fully connected layers. The first convolutional layer uses a 4-dimensional kernel $W^{1 \times 3 \times 26 \times 32}$ and a bias term $B^{32}$ to transform the input array $X^{128 \times 26 \times 8 \times 10}$ into a new array $y^{128 \times 8 \times 10 \times 32}$. This convolution operator slides 26×32=832 receptive fields (filters) of size 1×3 of the kernel W over the input array X and performs a series of dot products and additions as follows:

$$Y_{i,j,k,l} = \sum_{m=1}^{26} \sum_{n=1}^{3} W_{1,n,m,l} X_{i,j,k+n-1,n} + B_l. \quad \text{(Equation 1)}$$

where 1≤i≤128, 1≤j≤8, 1≤k≤10, 1≤l≤32 and the $3^{rd}$ dimension of is padded with 0's when needed. The purpose of convolution is to learn as many local features as possible through several different filters. Hence, the kernel W is often called "feature detector" and the output V is called "feature map". As can be seen from Equation 1, convolution was performed along the $3^{rd}$ dimension of X, i.e. the intensity window, to learn the bell-shape features, i.e. peaks. In some embodiments, different sets of filters were also used for different amino acids. This above is one preferred setting identified after trying multiple convolution combinations of ions and/or amino acids. Other settings or preferred settings are also possible with more data.

In some embodiments, the linear convolution is followed by an activation with Rectified Linear Unit (ReLU), i.e. f(x)=max(0,x). Activation functions are used to add nonlinearity (must have in each layer, add curve) into neural network models and ReLU is preferable because of its many advantages. Thus, the output Z of the first convolutional layer is obtained by applying the ReLU function on Y element-wise:

$$Z_{i,j,k,l} = \text{ReLU}(Y_{i,j,k,l}). \quad \text{(Equation 2)}.$$

The second convolutional layer is applied on top of the first convolutional layer in a similar way with another kernel $V^{1 \times 2 \times 32 \times 32}$. Adding more convolutional layers did not show significant improvement of accuracy, probably because the bell-shape features are not too complicated to learn. In some embodiments, max-pooling is also applied.

In some embodiments, the convolutional layers are followed by a fully-connected layer, or often called hidden layer, of 512 neuron units. As the name suggests, each unit is connected to every output of the previous convolutional layer to process all local features together. This is done via a linear matrix multiplication and addition as following:

$$Y_{hidden}^{128 \times 512} = \text{ReLU}(X_{hidden}^{128 \times 2,560} W_{hidden}^{2,560 \times 512} B_{hidden}^{512}). \quad \text{(Equation 3)}.$$

The output of the previous convolutional layer with shape 128×8×10×32 is first reshaped into $X_{hidden}^{128 \times 2,560}$ to be compatible with the matrix multiplication operator. ReLU is also applied element-wise after the linear operations.

The final fully-connected layer has 26 neuron units, which correspond to 26 symbols to predict. It is connected to the previous hidden layer in a similar way as Equation 3, except that there is no ReLU activation.

In one embodiment, the system also applies dropout; as used herein "dropout" a regularization technique for reducing overfitting in neural networks by preventing complex co-adaptations on training data. It is one way of performing model averaging with neural networks. Dropout was used after the second convolutional layer with probability 0.25 and after the first fully-connected layer with probability 0.5. The idea of dropout is that neuron units are randomly activated (or dropped) at every training iteration so that they do not co-adapt. At the testing phase, all units are activated and their effects are averaged by the dropout probability.

Figure 3:
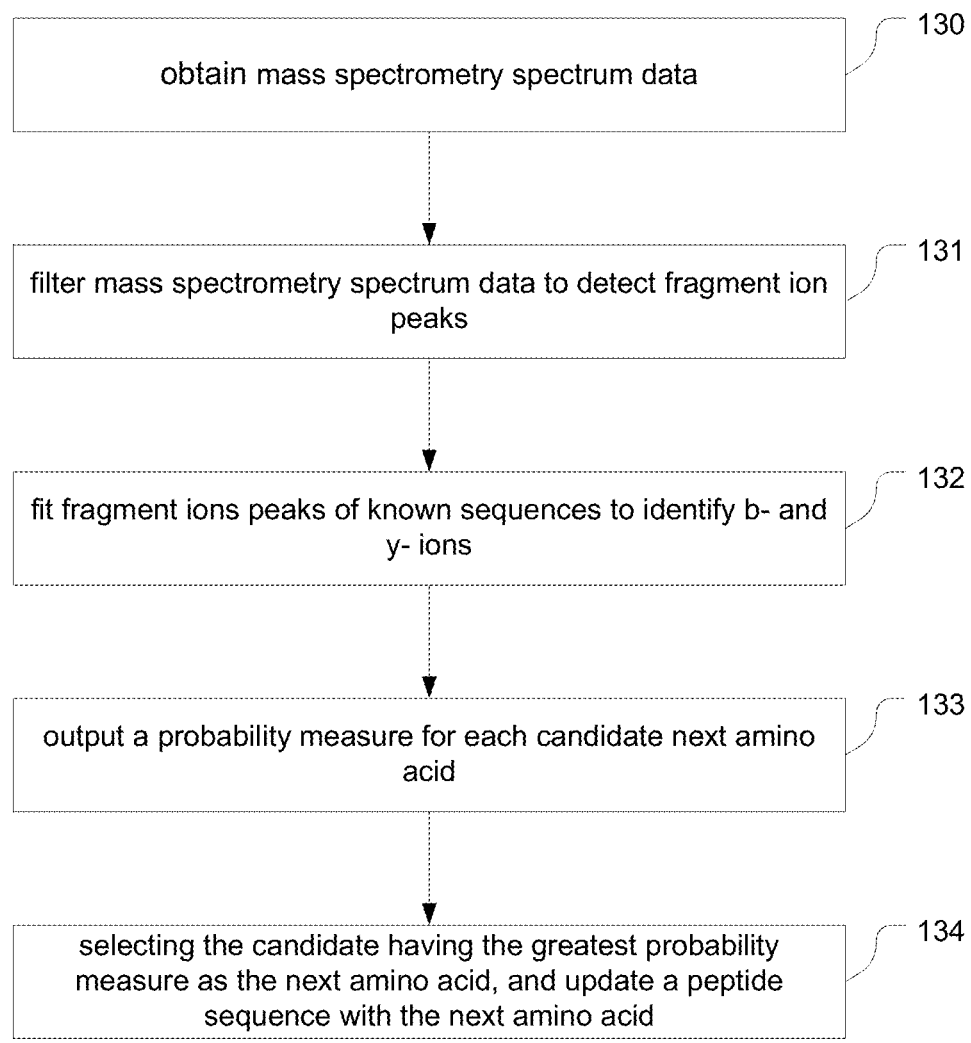
FIG. 3 is a flow chart of an example de novo sequencing procedure using neural networks, by identifying b- and y-ions.

Turning to FIG. 3, one embodiment of a de novo sequencing method is shown, using ion-CNN. A mass spectrometry spectrum data is obtained 130 and inputted into the system comprising a processor and at least one memory providing a plurality of layered nodes configured to form an ion-CNN. Given a staring sequence or given a sequence determined from a previous iteration, the plurality of layered nodes are used to filter the mass spectrometry spectrum data to detect fragment ion peaks in the mass spectrum 131, and then fit fragment ions peaks of known sequences to identify b- and y-ions 133. In some embodiments, the b- and y-ions of the current iteration and those corresponding to the next candidate amino acid in the sequence are identified by fitting. The ion-CNN outputs a probability measure for each candidate next amino acid 133. A candidate having the greatest probability measure is selected as the next amino acid, and peptide sequence is updated accordingly 134. In some embodiments, this method is iterated to determine the full peptide sequence.

A structure of ion-CNN is illustrated in FIG. 4 for DIA. In de novo sequencing for DIA, the role of the ion-CNN is to learn (i) 3D shapes along m/z and retention time dimensions of fragment ions and (ii) correlation between the precursor and its fragment ions (FIGS. 1A and 1B). The first input to the ion-CNN is a 5-dimensional fragment ions intensity array of shape (126, 26, 94 8, 5, 10), where:

the $1^{st}$ dimension is the batch size;
the $2^{nd}$ is the number of amino acids;
the $3^{rd}$ is the number of ion types;
the $4^{th}$ is the number of associated spectra; and
the $5^{th}$ is the model's window size.

Thus, for DIA data, there is the extra dimensionality of retention time where multiple associated spectra can be used to predict the peptide sequence of the precursor features. Moreover, the second input to the ion-CNN, a 2-dimensional array of shape (128, 5), is the MS1 intensity profile of the features over its retention time period.

Theoretically all the true fragment ions of the precursor feature should be correlated to the feature and to each other. The fragment ions should also form 3D shapes along the m/z and retention time dimensions (FIGS. 1A and 1B). Three convolutional layers followed by one max pooling layer and one fully-connected layer were used to learn those patterns (FIG. 4). For each layer RELU was chosen as the activation function. Eventually the fully-connected layer output a matrix of shape (128, 512). To let the model use information about the correlation between fragment ions and feature, the Pearson correlation was also calculated between the feature and its fragment ions and concatenated that indicator with the output of the fully-connected layer. For each 5-dimensional fragment ions intensity array I, the Ifrag was defined as the sum over the $3^{rd}$ and $5^{th}$ dimension. Thus Ifrag is a tensor of shape (128, 26, 5). Then the MS1 intensity profile matrix was repeated for 26 time and stacked together to obtain Iprof with size (128, 26, 5). Finally the correlation between Ifrag and Iprof was computed along their $3^{rd}$ axis. The resulting correlation tensor, with shape (128, 26), is then concatenated with the output of the fully-connected layer. The experiment showed that by including the correlation feature, DeepNovo's amino acid accuracy improves by 5.4%. In addition, it is easier to obtain overfitting with DIA than DDA data. Dropout layers were used after the final convolutional layer and the fully-connected layer.

Compared to the DDA data, it was found that more convolutional layers yielded better performance for DIA data. It was also found that max-pooling was very important in accounting for shift-invariance, especially along the retention time dimension.

Spectrum-CNN and LSTM

Some embodiments of DeepNovo comprises a long short-term memory (LSTM) network, which is one type of recurrent neural networks (RNNs). The LSTM model represents each amino acid class by an embedding vector, i.e, a collection of parameters that characterize the class (similar to word2vec). Given a prefix, the model looks for the corresponding embedding vectors and sequentially put them through the LSTM network. Moreover, DeepNovo also encodes the input spectrum and uses it to initialize the cell state of the LSTM network. For that purpose, the spectrum is discretized into an intensity vector that subsequently flows through another CNN, called spectrum-CNN, before being fed to the LSTM network.

The spectrum-CNN coupled with LSTM model is designed to learn amino acid sequence patterns of the peptide in association with the feature's spectra. The spectrum-CNN was used to encode the intensity vector of the spectra and the LSTM to decode the amino acids. This is similar to the idea of automatically generating a description for an image, where a convolutional neural network is used to encode, or to "understand", the image and a recurrent neural network is used to decode, or to "describe", the content of the image. The input to Spectrum CNN is 4-dimensional tensor of shape (128, 5, 150,000, 1), which is a batch of normalized feature matrices. The spectrum CNN consists of one max pooling layer, two convolution layers and one fully connected layer (FIG. 6). It encodes the input into an array $h_{init}$ of size (128, 512). Then DeepNovo initializes the LSTM module with zero states and feed $h_{init}$ to the LSTM to "warm up" its hidden state (FIG. 2). During the development for DeepNovo DIA model, it was also tested directly using $h_{init}$ as the initial state for the LSTM and both "warm up" methods lead to similar results. To keep the model consistent with the DeepNovo for DDA model, the original way was kept for initializing the LSTM.

Spectrum-CNN: Simple Version

The input to the spectrum-CNN is, for example, an array of shape 128×1×50,000×1, where 128 is the batch size, 50,000 is the size of intensity vectors given the maximum mass of 5,000 Da (peptide mass) and the resolution of 0.1 Da. As the input size is too large, DeepNovo first tries a simple version of spectrum-CNN that includes two convolutional layers, each with 4 filters of size 1×4, and one fully-connected layer of 512 neuron units. ReLU activation, max-pooling, and dropout are also used in the same way as for the ion-CNN described above.

It should be noted that the pattern recognition problem with tandem mass spectra here is quite different from traditional object recognition problems. Usually an object is recognized by its shape and its features (e.g. face recognition). However, in a tandem mass spectrum, an amino acid is identified by two bell-shape signals, i.e. peaks, whose distance between them has to precisely match with the amino acid mass. Because distance is involved, the simple spectrum-CNN and other common CNN models may not be sufficient.

Spectrum-CNN: Advanced Version

To take the distance into account, in one embodiment the system slices each input intensity vector into pieces based on the amino acid masses. For instance, given that the mass of Alanine, or "A", is 71.0 Da and the resolution is 0.1 Da, we slice the intensity vector from index 710 till the end to create a new vector. The system pads the new vector by 0's so that it has the same size as the original one and concatenate the two along the second dimension to obtain an array of shape 128×2×50,000×1. This procedure is repeated for all 26 symbols and construct a new input array of shape 128×2×50,000×26.

After pre-processing, the system applies the first convolutional layer with kernel of shape 2×10×26×32. The idea is to capture two bell-shape signals in the same filter of size 2×10. This is followed by another convolutional layer with kernel of shape 1×5×32×64 and one fully-connected layer of 512 neuron units. Again, ReLU activation, max-pooling, and dropout are also used. In some embodiments, max-pooling is used aggressively because the intensity vectors are very sparse.

It should be noted that the goal of the spectrum-CNN is not to make accurate prediction of the next amino acid as the ion-CNN. Instead, the spectrum-CNN only tries to pick up signals of which amino acids are presented in the spectrum and provide that information to the LSTM model to better learn sequence patterns of amino acids. In one embodiment, the spectrum-CNN output is a vector of size 512, corresponding to 512 neuron units of its fully-connected layer.

LSTM

Long Short Term Memory (LSTM) networks, one type of Recurrent Neural Networks (RNNs), has one application of which is for the handling of sequential data in Natural Language Processing and Speech Recognition. RNNs are called "recurrent" because they repeat the same computations on every element of a sequence and the next iteration depends on the networks' "memory" of previous steps. For example, one could predict the next word in a sentence given the previous words. In de novo peptide sequencing, embodiments of the system predicts the next amino acid (a symbol), given the previous ones (i.e. the prefix), based on the fact that amino acids do not just appear in a random order in protein sequences. Instead, proteins often have particular patterns in their sequences.

In some embodiments, a standard LSTM model is used, detailed of which are known to the skilled person and can be found in literatures such as [34,35,36] or online resources. Configurations of the LSTM used by the present system is described. First, DeepNovo uses embedding vectors of size 512 to represent each of 26 symbols, in a manner similarly to word2vec approach that uses embedding vectors to represent words in a vocabulary. The embedding vectors form a 2-dimensional array $Embedding^{26 \times 512}$. Thus, the input to the LSTM model at each iteration is a vector of size 512. Second, the output of the spectrum-CNN is used to initialize the LSTM model, i.e. being fed as the 0-input. Lastly, the LSTM architecture consists of 1 layer of 512 neuron units and dropout layers with probability 0.5 for input and output. The recurrent iterations of the LSTM model can be summarized as follows:

$$x_0 = CNN_{spectrum}(I)$$

$$x_{t-1} = Embedding_{a_{t-1}*}, t > 1$$

$$s_t = LSTM(x_{t-1})$$

where I is the spectrum intensity vector, $a_{(t-1)}$ is the symbol predicted at iteration t−1, $Embedding_{(i,*)}$ is the row i of the embedding array, and $s_t$ is the output of the LSTM and will be used to predict the symbol at iteration t,t=1,2,3, .... Similar to the ion-CNN model, the system also adds a fully-connected layer of 26 neuron units to perform a linear transformation of the LSTM 512 output units into signals of 26 symbols to predict.

LSTM networks often iterate from the beginning to the end of a sequence. However, to achieve a general model for diverse species, the present inventors found that it is better to apply LSTM on short k-mers. In some embodiments, further data allows for better optimization for using short k-mers, which the term as used herein refers to smaller units or substrings (k-mer) derived from the peptide in question, the k-mer substring having k-amino acid length.

Figure 5:
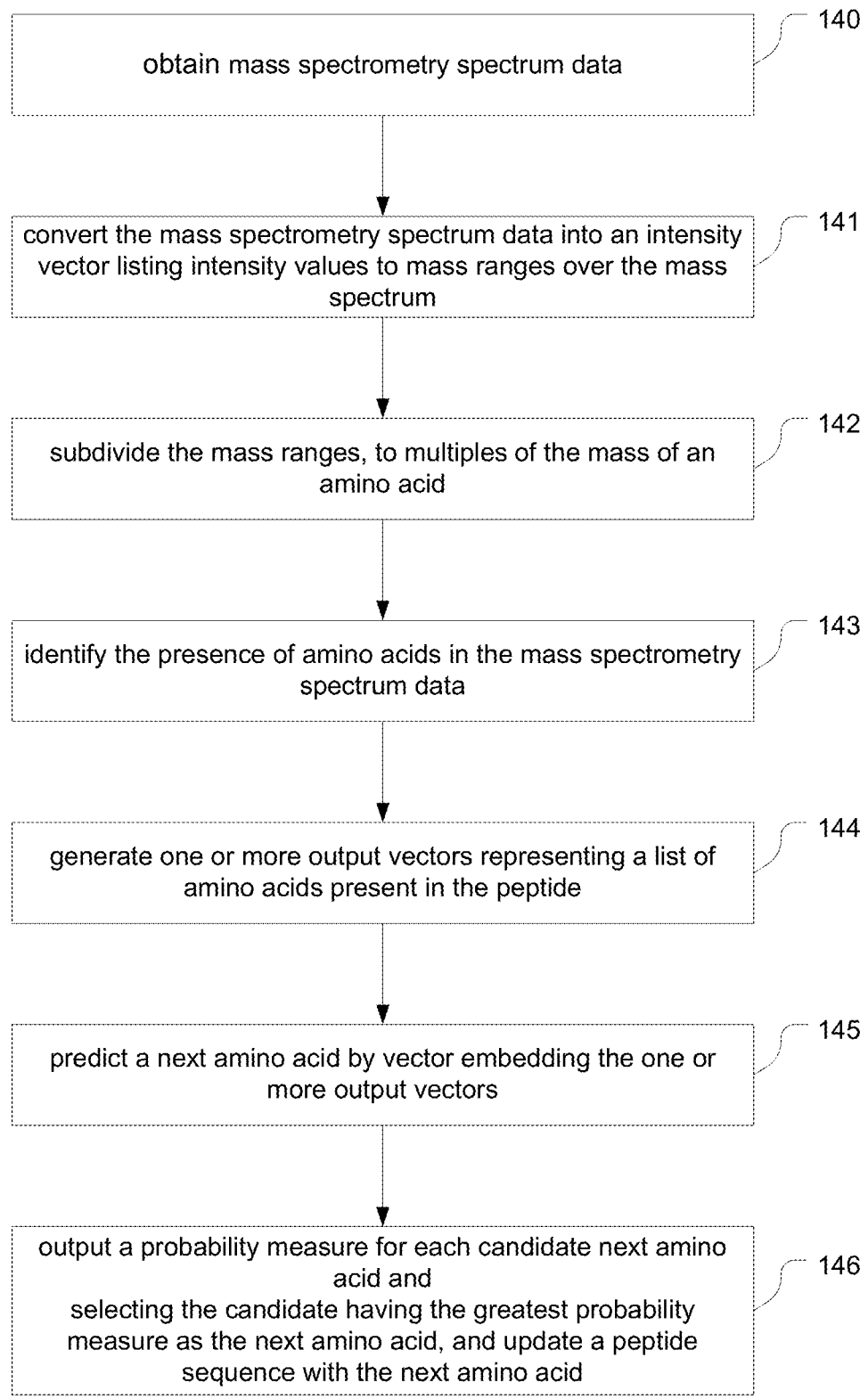
FIG. 5 is a flow chart of an example de novo sequencing procedure using neural networks, by predicting the next amino acid.

Turning to FIG. 5, one embodiment of a de novo sequencing method is shown, using spectrum-CNN and LSTM. A mass spectrometry spectrum data is obtained 140 and inputted into the system comprising a processor and at least one memory providing a plurality of layered nodes configured to form an ion-CNN. Optionally, the mass spectrometry spectrum data is converted into an intensity vector listing intensity values to mass ranges over the mass spectrum 141. Optionally, the intensity vector is sliced by subdividing the mass ranges to multiples of the mass of an amino acid 142. For example, the sliced intensity vector is represented as an array listing intensity values to ranges of masses that are multiples of the mass of an amino acid. The array further lists intensity vectors for each possible amino acid. Given a staring sequence or given a sequence determined from a previous iteration, the plurality of layered nodes are used to identify the next amino acid in the sequence. The presence of amino acids in the mass spectrometry spectrum data is identified 143, and one or more output vectors are generated representing a list of amino acids present in the peptide 144. The next amino acid in the sequence is predicted by vector embedding the one or more output vectors 145. The spectrum-CNN and LSTM output a probability measure for each candidate next amino acid, and a candidate having the greatest probability measure is selected as the next amino acid, and peptide sequence is updated accordingly 146. In some embodiments, this method is iterated to determine the full peptide sequence.

Integrating Ion-CNN and LSTM

In some embodiments that combine the ion-CNN and LSTM, the system first concatenates the outputs of their second-to-last layers, each of size 512, to form a vector of size 1024. Then the system adds a fully-connected layer of 1024 neuron units with ReLU activation, dropout with probability 0.5, and followed by another fully-connected layer of 26 neuron units to perform a linear transformation into signals of 26 symbols to predict. Thus, the final output of DeepNovo neural networks is a vector of 26 signals, often called logits (unscaled log probabilities). This logits vector will be further used to calculate the loss function during training or to calculate the prediction probabilities during testing.

In some embodiments, all weight and bias parameters, i.e. W's and B's, of the CNNs, embedding vectors, and parameters of the LSTM will be estimated and optimized during the training process. In one embodiment, DeepNovo performs bi-directional sequencing and uses two separate set of parameters, forward and backward, except for the spectrum-CNN and the embedding vectors. The hyper-parameters, such as the numbers of layers, the numbers of neuron units, the size of embedding vector, the dropout probabilities, the number and types of fragment ions, etc. can be configured to define an instance of DeepNovo model.

The outputs of ion-CNN and LSTM are combined to produce a probability distribution over the amino acid classes. The next amino acid can be selected as the one with the highest probability or can be sampled from the distribution. Moreover, given the peptide mass and the prefix mass, DeepNovo calculates the suffix mass and employs knapsack dynamic programming to filter out those amino acids whose masses do not fit the suffix mass. This helps guarantee that final candidate sequences will have the correct peptide mass. Combining all together, DeepNovo then performs beam search, a heuristic search algorithm that explores a fixed number of top candidate sequences at each iteration, until it finds the optimum prediction.

Training Techniques

Focal Loss Function

Previously for DeepNovo DDA model, cross entropy loss was used as the loss function. In the present DIA model, a proposed loss function was used, called focal loss [12] and the experiment showed that by switching to focal loss, DeepNovo's performance significantly improved. Lin et al. (2017) proposed focal loss to solve the class imbalance issue in object detection. In object detection problems, the neural networks need to classify whether a patch of image is an object or background. Due to the nature of this problem most patches the neural networks could see are background and this cause problems for end to end training with cross entropy loss. To deal with this problem, Lin et al. (2017) proposed a dynamically scaled cross entropy loss which they named focal loss. For a binary classification problem, $y \in \{0, 1\}$ was denoted as the ground truth class for a data point, and p as the model's predicted probability for class 1. Then the focal loss is defined by the following formula:

$$Focal\ Loss = -(1-p_t)^\gamma \log(P_t)$$

where $p_t=p$ if y is class 1 and $p_t=1-p$ if y is class 0, γ is a hyperparameter greater than 1.

From the formula above, it can be seen that, compared to cross entropy loss, focal loss scales down the loss by a ratio of $(1-p_t)^γ$. This means that focal loss down weights the contribution of easy examples (where $1-p_t$ is small), therefore the model would focus more on hard examples.

In this case, it was found that the DeepNovo model also suffered from class imbalance problem since the frequency for amino acids varied a lot. Therefore, focal loss was selected to better train the DeepNovo model. During training, the activation function of last layer was changed from softmax function to sigmoid function thus the model will give a probability between 0 and 1 for each of the 26 classes (note that here the sum of these 26 probabilities might not equal 1). Then for each class the binary classification focal loss could be computed for each class using the above formula and the average of those 26 losses was used as the final loss. At inference time the activation function was switched back to softmax as this was found to lead to better performance.

Another problem with training data is that the labels were noisy, since peptides found by database search algorithm was used as the ground truth. For example, suppose the database search returns peptide 'PEPTLDE' for a feature, then for de novo sequencing one is not very confident about the $5^{th}$ amino acid since changing L to I might lead to similar MS/MS spectra. If for the $5^{th}$ amino acid DeepNovo predicts 0.5 probability for "I" and 0.5 probability for "L", then under cross entropy loss DeepNovo will receive a big penalty since the predicted probability for ground truth is far from 1.0. However under focal loss the penalty will be smaller. In this case focal loss also helps to relieve the problem of noisy target. The experiments show that by training with focal loss, the amino acid accuracy increase about 20% on the plasma dataset.

Model Training

DeepNovo was trained on a DIA dataset of urine samples from 64 patients published previously [14]. The training dataset includes 2177667 spectra, 202114 labeled features, and 14400 unique peptides (See Table 1). The data was divided into three sets: training, validation, and testing, with ratio 90%, 5%, and 5%, respectively. For de novo sequencing purpose, the training, validation, and testing sets did not share common peptides. During the training process, early stopping was used, i.e. periodically evaluating the model and only saving it if there was improvement on the validation set. It was found that DIA data was easier to become over-fitted than DDA data, and usually the training process stopped after about 5 epochs. To train the model adam algorithm was used with the suggested hyperparameters $β_1=0.9$, $β_2=0.999$ and a fixed learning rate of 0.001. To prevent the gradient exploding problem, for each batch the gradient was clipped so that the global L2 norm of the gradient tensor is less than 5.

DeepNovo was evaluated on two other sets of different patients that have been diagnosed with ovarian cyst (OC, 6 patients) and urinary tract infections (UTI, 6 patients). DeepNovo was also tested on a dataset of plasma samples from another study [10]. Those three testing datasets were not used during model development. (See Table 1)

TABLE 1

Summary of training and testing datasets in the study. Note that labeled features and unique peptides refer to in-house database search results. For de novo sequencing results, please check the main text.

|  | No. of samples | No. of spectra | No. of all features | No. of labeled features | No. of unique peptides |
|---|---|---|---|---|---|
| Training dataset |  |  |  |  |  |
| Pain control group | 64 | 2177667 | 1674376 | 202114 | 14400 |
| C1R-Madrid | 1 | 80512 | 10164 | 1390 | 1075 |
| Testing datasets |  |  |  |  |  |
| Ovarian Cyst | 6 | 203780 | 143763 | 16301 | 5016 |
| UrinaryTract Infection | 6 | 206477 | 163274 | 21103 | 7209 |
| Plasma | 12 | 1097400 | 29562 | 7673 | 3328 |
| Jurkat-Oxford | 3 | 307704 | 47047 | 1308 | 647 |

Methods for Data Analysis

The list of precursor features, DIA spectra, and de novo predictions that was used for data analysis have been uploaded to MassIVE database, accession number MSV000082368.

Precursor Feature Detection

For precursor feature detection from LC-MS map, an existing peak caller was used from Zhang, J. et al. (2012). Other peak callers, e.g. MaxQuant, can also be used in this role. The output of this step is a list of precursor features, each of which should include the following information: feature id, m/z, charge, abundance level (area), retention time range (begin & end), intensity values over the retention time range. Moreover, given the m/z and retention time range of a feature, all MS/MS spectra were collected so that they are within the feature's retention time range and their DIA m/z windows must cover the feature's m/z. For example, a CSV file showing all precursor features detected from a dataset contain the following information organized in columns:

- "spec group": the feature id; "F1:6427" means feature number 6427 of fraction 1.
- "m/z": the mass-to-charge ratio.
- "z": the charge.
- "rt_mean": the mean of the retention time range.
- "seq": the column is empty when running de novo sequencing. In training mode, it contains the peptides identified by the in-house database search for training.
- "scans": a list of all MS/MS spectra collected for the feature as described above; the spectra's identification numbers are separated by semicolon; for example, an identification number of "F1:101" means scan number 101 of fraction 1; the spectra's identification numbers can be used to locate the spectra in a corresponding mass spectrometer file, for example, a MGF file.
- "profile": intensity values over the retention time range; the values are pairs of "time:intensity" and are separated by semicolon; the time points align to the time of spectra in the column "scans".
- feature_area: precursor feature area estimated by the feature detection.

In-House Database Search

To generate the training data for DeepNovo, an in-house database search tool was built for DIA data. First, from each precursor feature and its associated MS/MS spectra, a pseudo-spectrum was generated. In particular, the Pearson correlation coefficient was calculated between the LC eluting profiles of the precursor and MS/MS fragment ions.

Then, fragment ions were selected that have Pearson correlation coefficient above 0.6 and used up to 500 most correlated ones to form the pseudo-spectrum.

The pseudo-spectra and the corresponding precursor information like m/z, charge were then searched against the UniProt/Swiss-Prot human database. This step can be done with any conventional DDA database search engines, such as PEAKS DB [13] was used in this case. Common parameter settings were used, such as: trypsin digestion, fixed modification C(Carbamidomethylation), precursor mass tolerance 30 ppm, fragment mass tolerance 0.02 Da for the plasma dataset. For HLA datasets, non-enzyme digestion, no modification, 20 ppm and 0.05 Da were used. The peptides were identified at 1% FDR cut-off were then assigned to the corresponding precursor features and were used as labels for training.

Post-Processing Analysis
Calculate Sequencing Accuracy for Labeled Features

For each labeled feature, the de novo peptide predicted by DeepNovo is compared to the ground-truth sequence identified by the database search. A simple way to do this is based on exact sequence matching. However, it is very common for de novo peptides to have 1-2 sequencing errors like swapping, or different amino acid combinations with the same mass. Hence, sequencing accuracy was calculated based on the alignment of their mass fragments [11]. The sequencing accuracy was measured at the amino acid level, that is, the ratio of the total number of matched amino acids over the total length of predicted peptides, and at the peptide level, that is, the fraction of fully-matched peptides (see FIGS. 7A-7D).

Filter High-Confidence De Novo Predictions

Figure 7A:
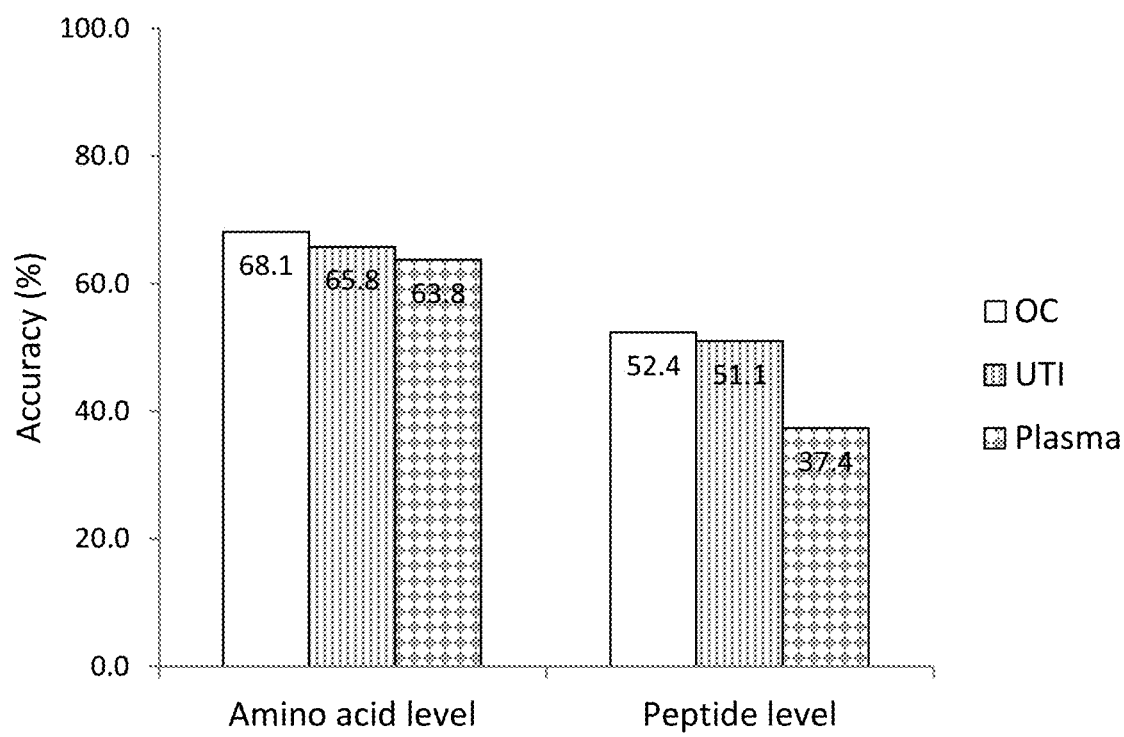
FIG. 7A-I shows evaluation results of DeepNovo on three datasets: Ovarian Cyst (OC), Urinary Tract Infection (UTI), and Plasma.
Figure 7B:
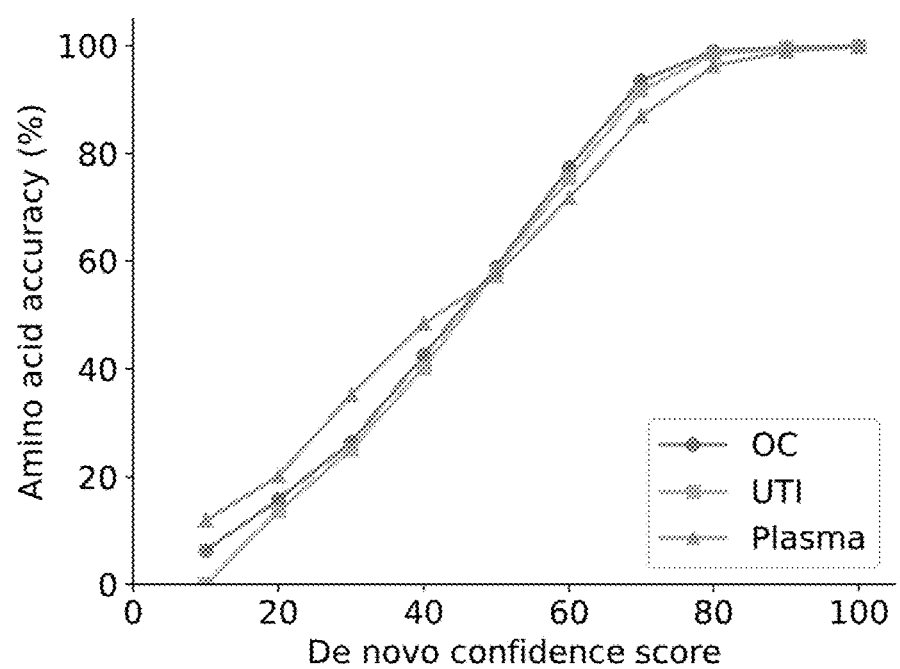
Figure 7C:
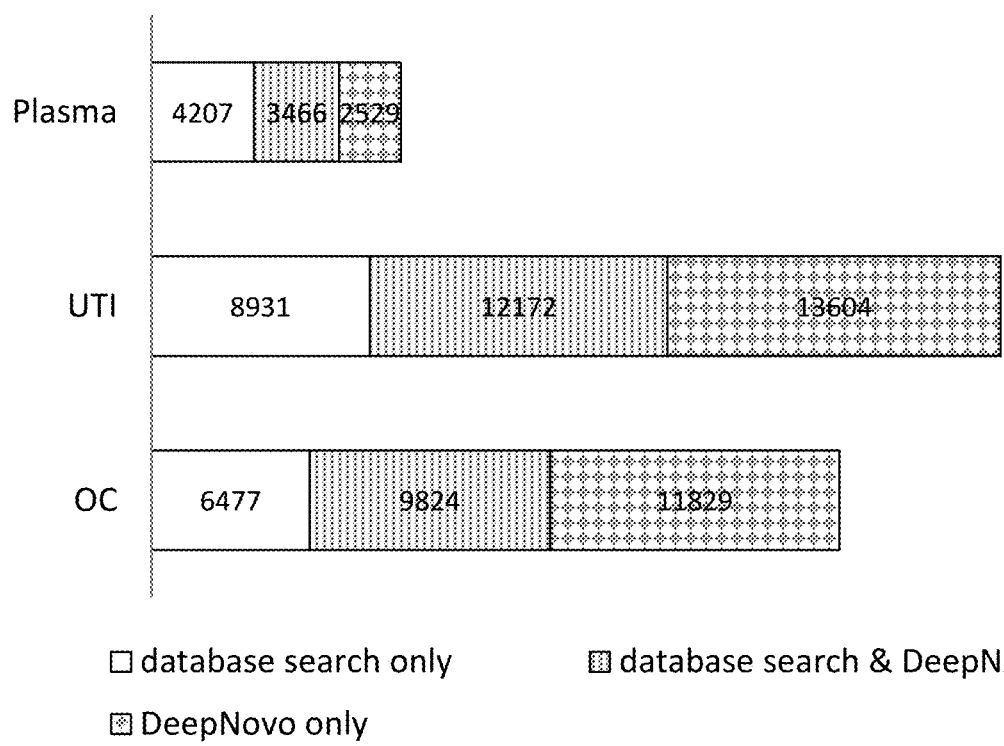
Figure 7D:
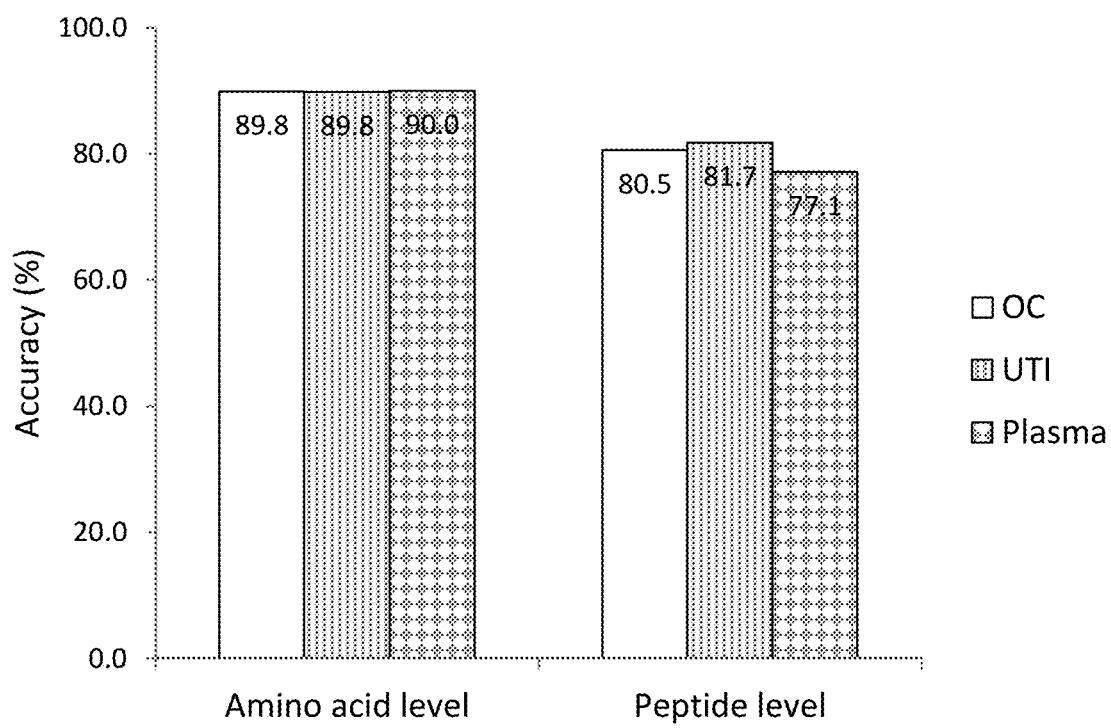

The confidence score of a peptide sequence is the sum of its amino acids' scores. The score of each amino acid is the log of the output probability distribution, i.e., the final softmax layer of the neural network model, at each sequencing iteration. The score was trained using only the training dataset. When applied to a new specific dataset, in some cases cut-off was selected to filter the de novo results of that dataset. This is similar to the case of database search, when setting 1% FDR, the cut-off score changes from one dataset to another. However, there is no such target-decoy method to estimate FDR for de novo sequencing. Hence, database search and de novo results were compared on their overlapping features, calculated de novo accuracy from above, and plotted the distribution of de novo confidence score with respect to de novo accuracy (FIG. 7B). Then, from the distribution, a cut-off of de novo confidence score was selected so that the de novo accuracy is 90% at amino acid level on the overlapping features. Finally, that cut-off was applied to de novo results of all features.

Filter De Novo Peptides Using Augmented-Database Search

The selection of high-confidence de novo predictions from above does not provide a way to control FDR. Thus, de novo peptides can be validated using the following approach. The original database fasta file was augmented with the de novo peptides identified by DeepNovo. Then, the database search were re-run using the new fasta file, other parameters remain unchanged. Finally, only de novo peptides that passed 1% FDR after re-run were selected. This analysis was performed in the in-house database search and Spectronaut. It was found that about 56.8% (1,143/2,011=56.8%) of de novo peptides passed 1% FDR for the plasma dataset. Such peptides should be supported by significant peptide-spectrum matches and co-elution profiles between precursors and fragment ions.

Post-Processing Analysis

Three different database search tools were used to validate the de novo results of DeepNovo.

Comparison of DeepNovo, PECAN and Spectronaut on the Plasma Dataset

The results of DeepNovo on the plasma dataset were compared against those reported in the original PECAN study of Ting et al., (2017), as well as against Spectronaut, a commercial software widely used for DIA analysis. While DeepNovo is a de novo sequencing system and PECAN, Spectronaut are based on database search, this comparison shows: (i) the accuracy of de novo sequencing (based on overlapping identifications) and (ii) new peptides identified by DeepNovo but not in the database.

PECAN reported 3,689 unique peptides from the plasma dataset, the results were retrieved from the original paper (Ting et al., 2017). Spectronaut was run using their direct DIA workflow with trypsin digestion, fixed modification C(Carbamidomethylation), variable modification M (Oxidation), and 1% FDR. Spectronaut reported 2,775 unique peptides. DeepNovo was run on the plasma dataset and selected high-confidence identifications based on the distribution of de novo confidence scores (See FIG. 7B). DeepNovo identified 4,291 unique peptides for 5,995 precursor features. Note that high-confidence de novo peptides may still contain sequencing errors, causing an increased number of unique peptides identified by DeepNovo, in which case validation should be conducted carefully.

Figure 8:
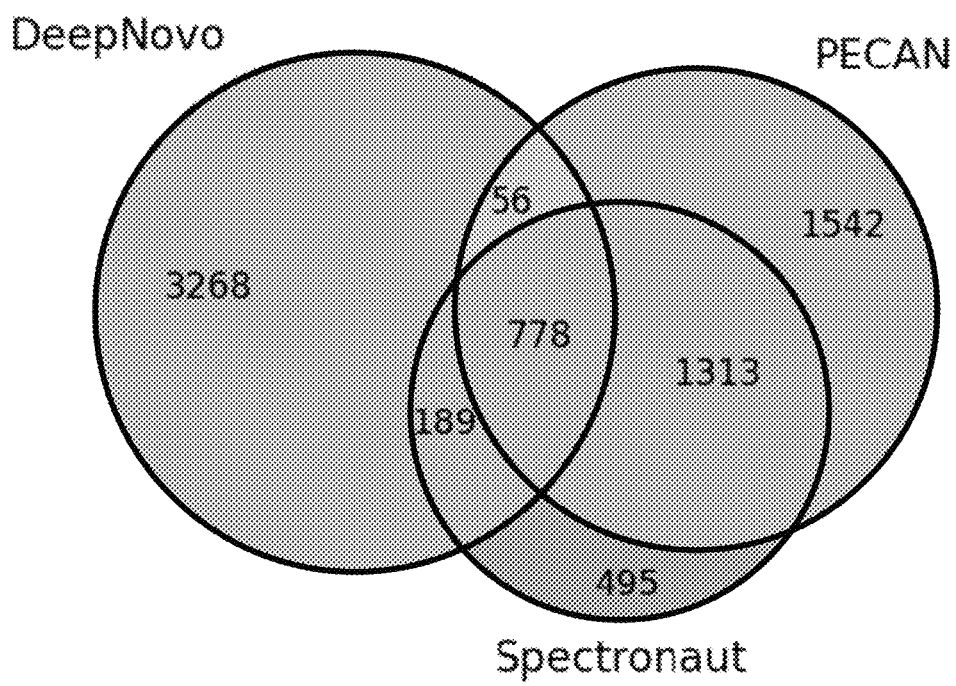
FIG. 8 shows a Venn diagram showing comparison of unique peptides identified by DeepNovo, PECAN, and Spectronaut from the plasma dataset. The number of 3,268 de novo peptides reported here by DeepNovo are before validation.

FIG. 8 shows the Venn diagram of DeepNovo, PECAN, and Spectronaut. The two database search methods reported 4,373 unique peptides in total, and DeepNovo correctly predicted the full sequences of 1,023 of them (23.4%). There are 2,091 peptides reported by both PECAN and Spectronaut, which can be considered as high-quality, and DeepNovo identified 778 of them (37.2%). Note that unlike database search, it is difficult for de novo sequencing to correctly predict the full sequence of a peptide due to swapping amino acids, combinations of the same mass, instrument errors/resolution, etc. Even for DDA data, state-of-the-art de novo sequencing tools typically achieve about 25-40% accuracy at the full peptide level, 60-70% at the amino acid level (Tran et al., 2017).

Figure 7E:
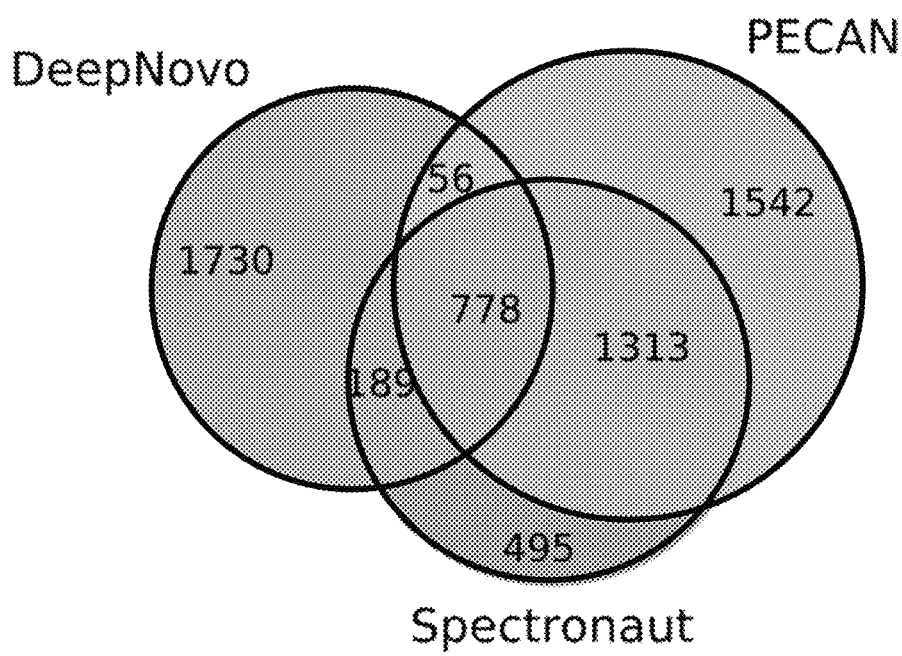

FIG. 8 shows 3,268 peptides reported only by DeepNovo, but they may contain de novo sequencing errors and require further investigation. First, if DeepNovo and the in-house database search reported peptides for the same precursor feature, the database peptide was considered as ground-truth and removed the DeepNovo peptide if it contained errors. 587 DeepNovo peptides were found identical to the corresponding database search result and removed 670 DeepNovo peptides with errors. 2,011 peptides were left remaining (3,268−587−670=2,011). To validate if these remaining peptides can be supported by significant peptide-spectrum matches, those 2,011 peptides were added to the database fasta file and re-run using the in-house database search. 1,143 peptides were obtained that passed 1% FDR threshold. Thus, the number of peptides reported only by DeepNovo was refined from 3,268 to 1730, of which 587 belong to the database and 1,143 are de novo peptides (see FIG. 7e).

The validation was repeated with the augmented fasta file using Spectronaut as the database search engine. 905 of 2,011 peptides passed 1% FDR threshold of Spectronaut. Among them, 744 peptides passed 1% FDR threshold of both Spectronaut and the in-house database search.

Figure 7F:
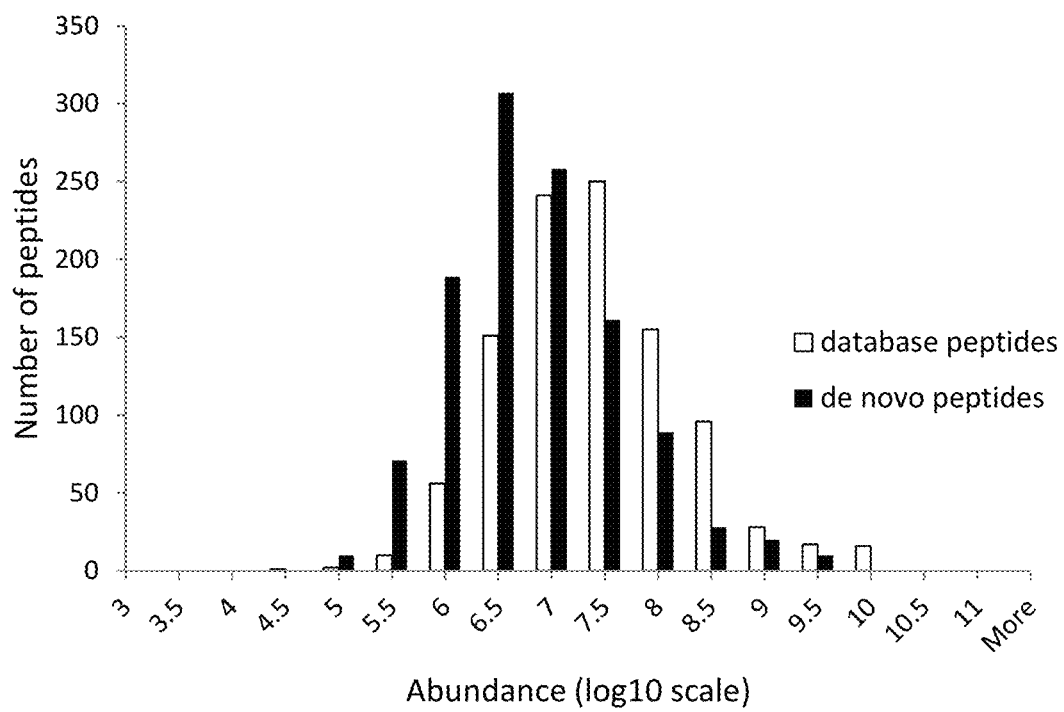
Figure 9:
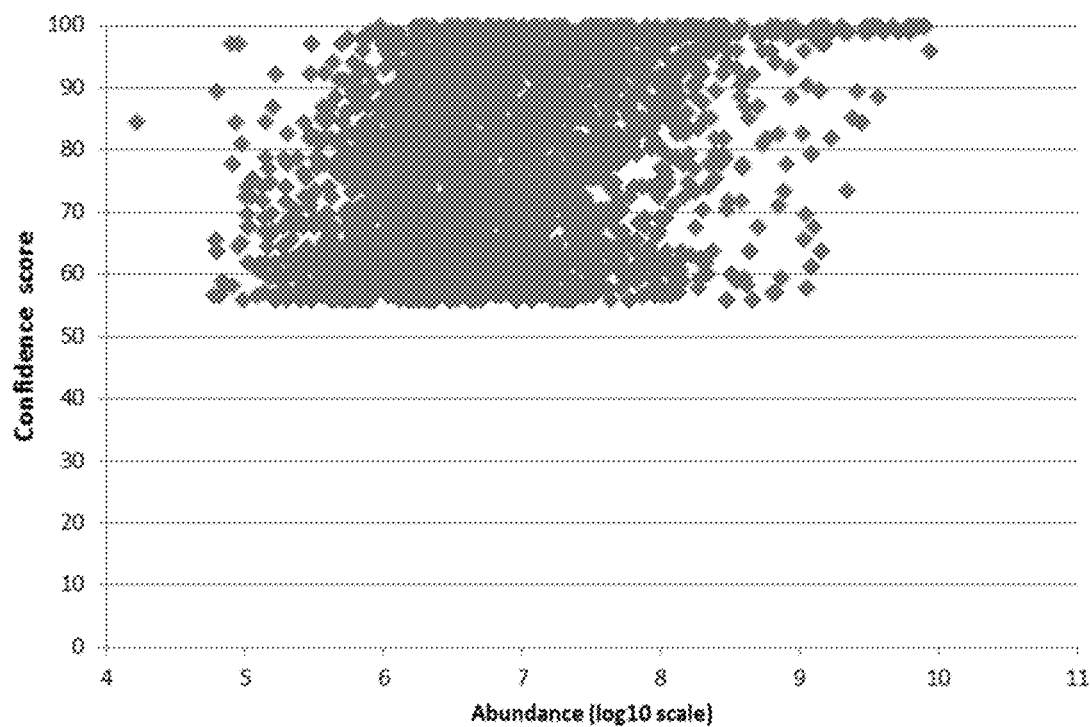
FIG. 9 shows the distribution of de novo confidence score versus peptide abundance of all peptides reported by DeepNovo from the plasma dataset.
Figure 10:
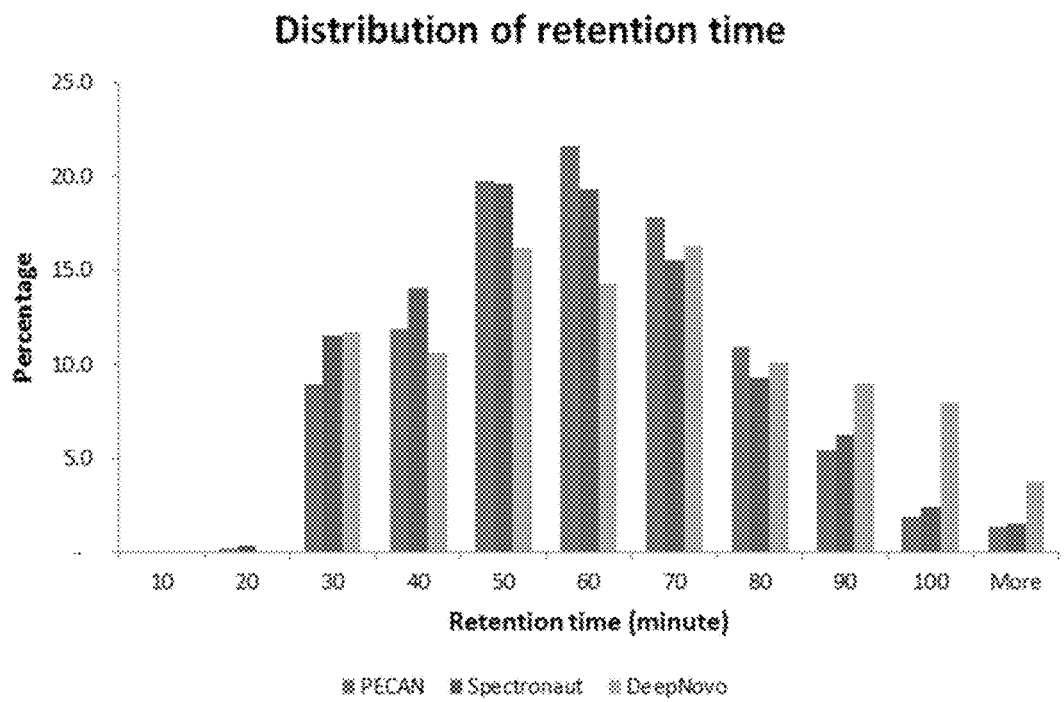
FIG. 10 shows a bar graph representing the distribution of retention times of 1,143 de novo peptides reported by DeepNovo and database peptides reported by PECAN and Spectronaut from the plasma dataset. For each set of three bars, the left bar is PECAN, middle bar is Spectronaut, right bar is DeepNovo.
Figure 11:
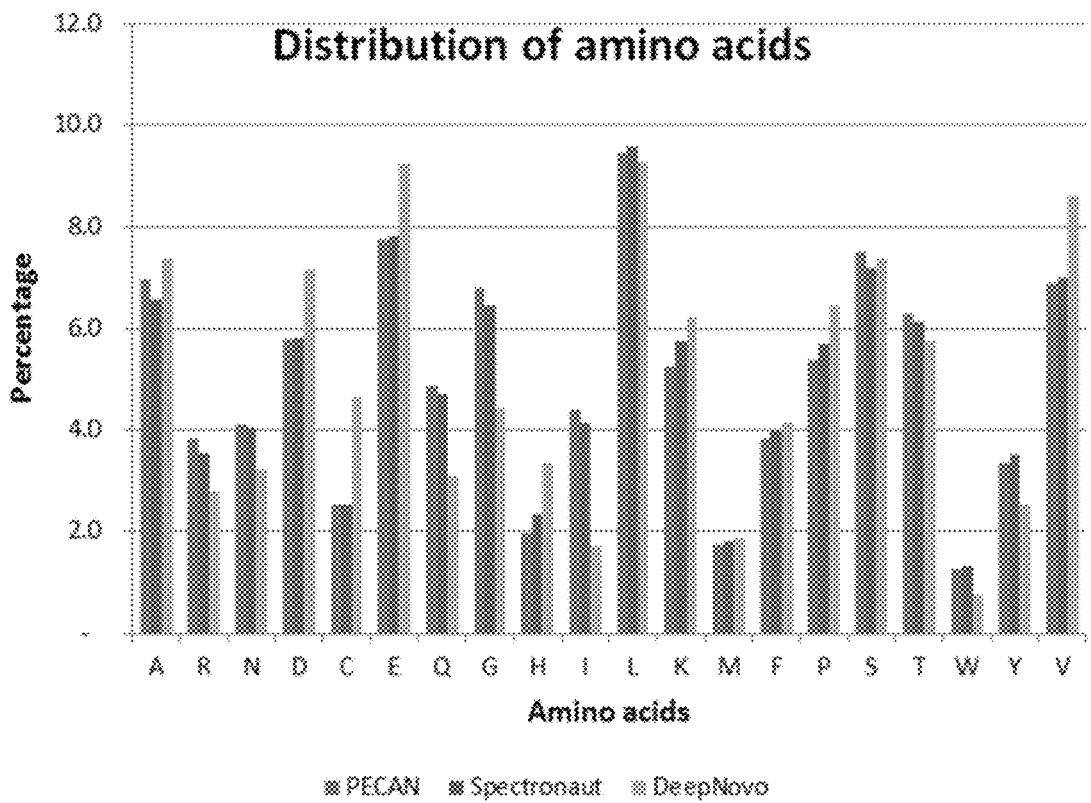
FIG. 11 shows a bar graph representing the distribution of amino acids of 1,143 de novo peptides reported by DeepNovo and database peptides reported by PECAN and Spectronaut from the plasma dataset. For each set of three bars, the left bar is PECAN, middle bar is Spectronaut, right bar is DeepNovo.

FIG. 7f shows the abundance distribution of 1,143 de novo peptides versus 1,023 database peptides identified earlier by DeepNovo and PECAN or Spectronaut. The abundance was determined as the precursor feature area by our precursor feature detection. It can be seen from FIG. 7f that the abundance of database peptides recovered by Deep-Novo spans from $10^5$ to $10^{10}$, demonstrating the performance of DeepNovo across multiple levels of abundance. The distribution of de novo peptides shows a shift towards lower abundance than database peptides. For instance, there are 270/1,143 (23.6%) de novo peptides that have abundance less than or equal $10^6$, as compared to 69/1,023 (6.7%) database peptides. These results demonstrate the ability of DeepNovo to identify low-abundance, de novo peptides. The distribution of de novo confidence score versus peptide abundance is shown in FIG. 9. The distributions of retention times and amino acid frequencies of 1,143 de novo peptides identified by DeepNovo are shown in FIGS. 10 and 11, and compared to database peptides identified by PECAN and Spectronaut. No significant systematic bias of the de novo peptides identified by DeepNovo was observed.

Next, BLAST was run on the 1,143 de novo peptides against the broad NCBI human non-redundant protein database to find supporting evidence from previous studies. 463 peptide matches were found with more than 90% identity. 123 de novo peptides that have BLAST hits of 100% identity were further investigated for supporting evidence from previous studies. 113 peptides were found belong to variable regions of immunoglobulin light and heavy chains (raw data not provided). 6 peptides were also found with human natural variants (raw data not provided). It is noted that such variable peptides change from one individual to another and cannot be found by the database search approach, thus illustrating the high versatility and performance of de novo sequencing.

Figure 12:
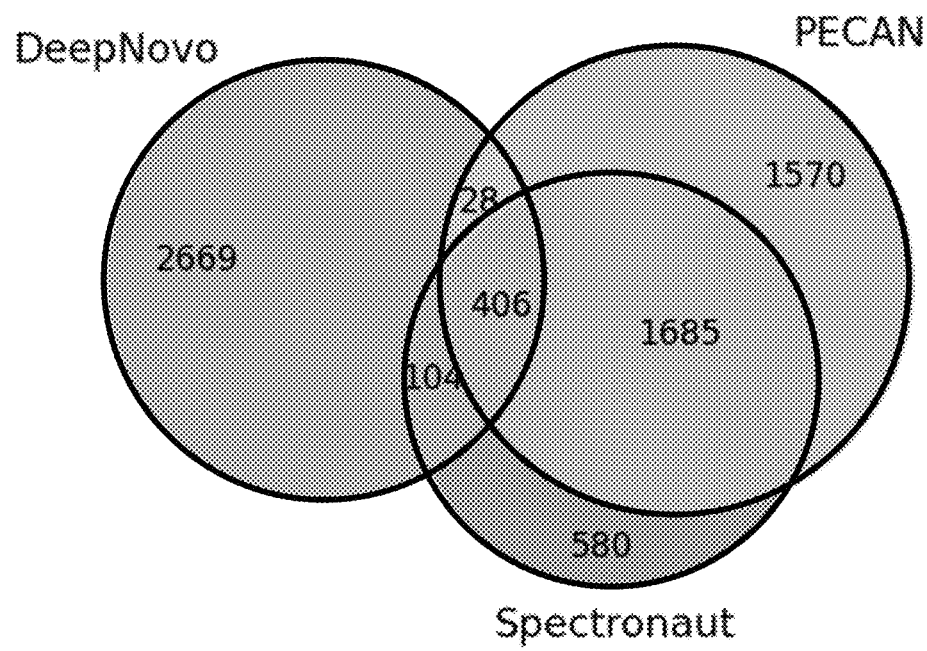
FIG. 12 shows a Venn diagram of unique peptides identified by DeepNovo, PECAN, and Spectronaut from the plasma dataset. (A) Original model trained with the urine dataset. (B) Model re-trained with part of the plasma dataset. Features that were used to re-train the model were removed from DeepNovo. DeepNovo peptides have not been filtered by sequencing errors and augmented database search.
Figure 12:
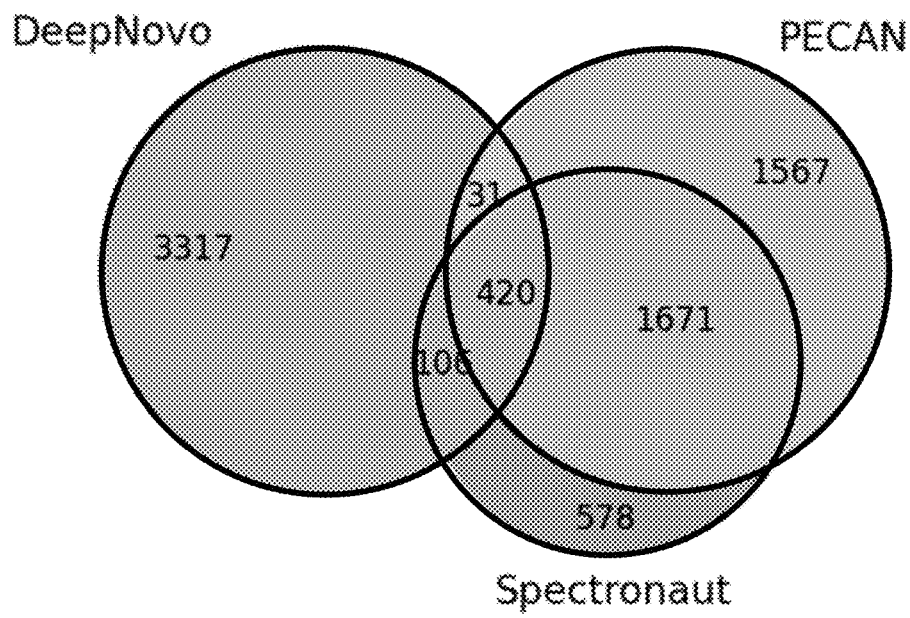

Similarity between training data and validation data was reduced as much as possible, to avoid any potential bias. Hence DeepNovo was trained on the urine dataset from Muntel et al. (2015) and validated on the plasma dataset from Ting et al. (2017). For example, DeepNovo was trained on half of the plasma dataset and the analysis was repeated again. Note that when re-running de novo sequencing, those precursor features that had been used to re-train DeepNovo were removed, so that training and validation did not share common features. FIG. 12 shows that the re-trained model has 3.5% more overlapping peptides with PECAN or Spectronaut (557/538=3.5%) and 24.3% more unique peptides (3317/2669=24.3%) than the original model.

Comparison of DeepNovo, PECAN and Spectronaut on the HLA Dataset

DeepNovo is used to identify novel peptides from human leukocyte antigen (HLA) dataset from Caron et al. (2015), which contain HLA peptides and were run on Sciex instrument which are very different from the training data from Muntel et al. (2015). DeepNovo was re-trained on part of the HLA datasets. In particular, Caron et al. includes 4 datasets from different cell types and research labs. DeepNovo was re-trained on the dataset C1R-Madrid University and validated on the dataset Jurkat-Oxford University. The dataset C1R-Madrid University is small. Only 1,390 labeled features with 1,075 peptides were identified by the in-house database search. Such amount of data was not enough to train a new model from scratch, so the existing model was re-trained with that data.

Figure 13:
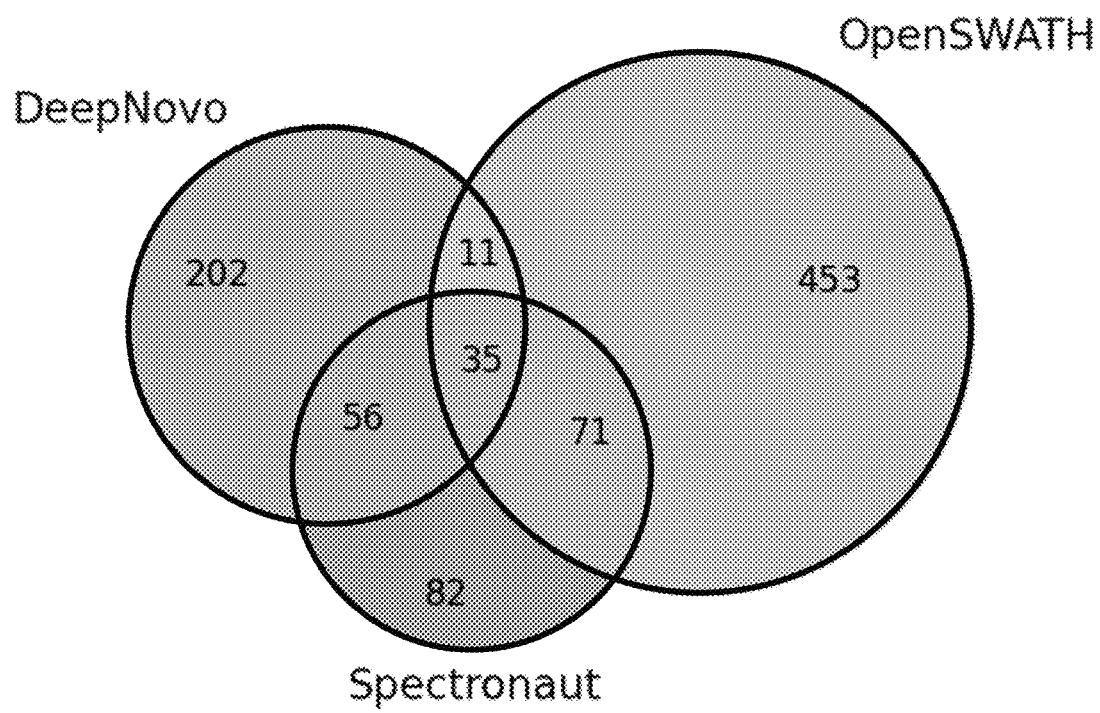
FIG. 13 shows a Venn diagram of unique peptides identified by DeepNovo, OpenSWATH, and Spectronaut from the dataset Jurkat-Oxford University.

The results of DeepNovo, OpenSWATH, and Spectronaut were compared on the dataset Jurkat-Oxford University. FIG. 13 shows the Venn diagram of unique peptides identified by the three tools. DeepNovo correctly predicted the full sequences of 102 database peptides that were reported by OpenSWATH or Spectronaut. Among 106 peptides reported by both OpenSWATH and Spectronaut, which can be considered as high-quality, DeepNovo identified 35 of them (33.0%). Among 202 peptides reported only by Deep-Novo, 72 can be found in the database, the remaining 130 are de novo peptides. Those 130 de novo peptides have also been filtered using the augmented-database search with 1% FDR, as described above for the plasma dataset. The original number of de novo peptides was 479.

Figure 14:
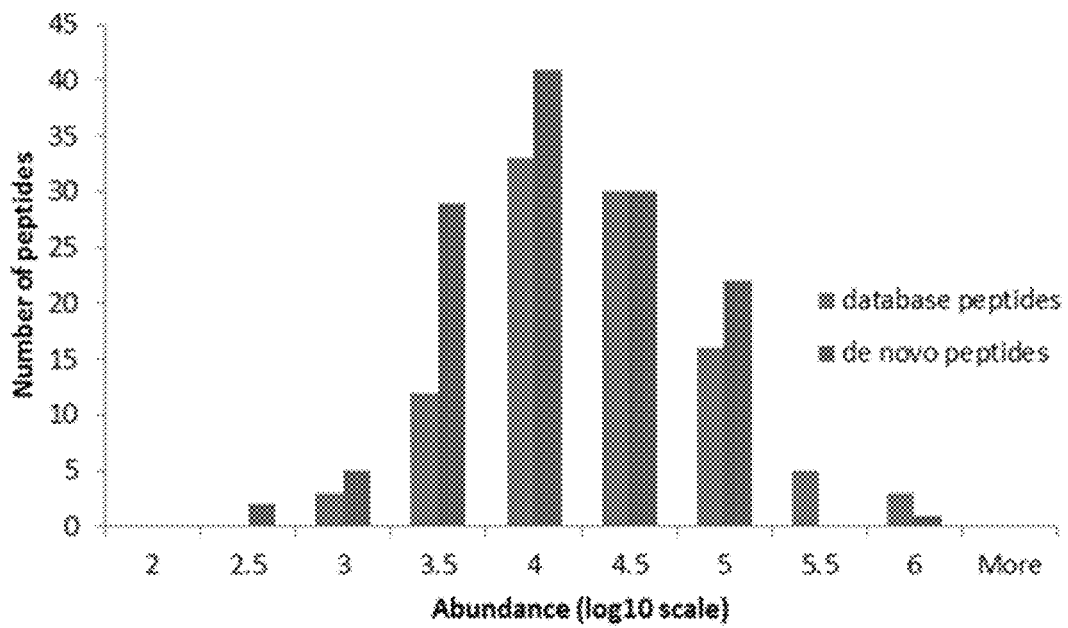
FIG. 14 shows a bar graph representing the abundance distribution of 130 de novo peptides versus 102 peptides identified by DeepNovo and OpenSWATH or Spectronaut from the dataset Jurkat-Oxford University. For each pair of bars, left bar is database peptide (OpenSWATH or Spectronaut), and right bar is de novo peptides (DeepNovo).

FIG. 14 shows the abundance distribution of 130 de novo peptides versus 102 peptides identified by DeepNovo and OpenSWATH or Spectronaut. More de novo peptides with low abundance were found than database peptides. For instance, there are 36/130 (27.7%) de novo peptides that have abundance less than $10^4$, as compared to 15/102 (14.7%) database peptides. In one example, 12 annotated spectra with low-abundance (precursor feature area of about $10^3$) were identified, which are novel HLA peptides that were predicted by DeepNovo but not identified by either OpenSWATH nor Spectronaut. Each peptide is supported by annotated fragment ions and co-elution profiles of precursor and fragment ions.

These results demonstrate the application of DeepNovo for de novo sequencing of HLA peptides from DIA data. This experiment also shows DeepNovo's performance on a variety of DIA instruments and data, including Thermo Q-Exactive HF and Sciex Triple TOF instruments, tryptic and HLA peptides. As such, the DIA de novo sequencing systems and methods provided herein greatly contributes to the field of mass spectrometry and its potential impact to immunotherapy.

Figure 7G:
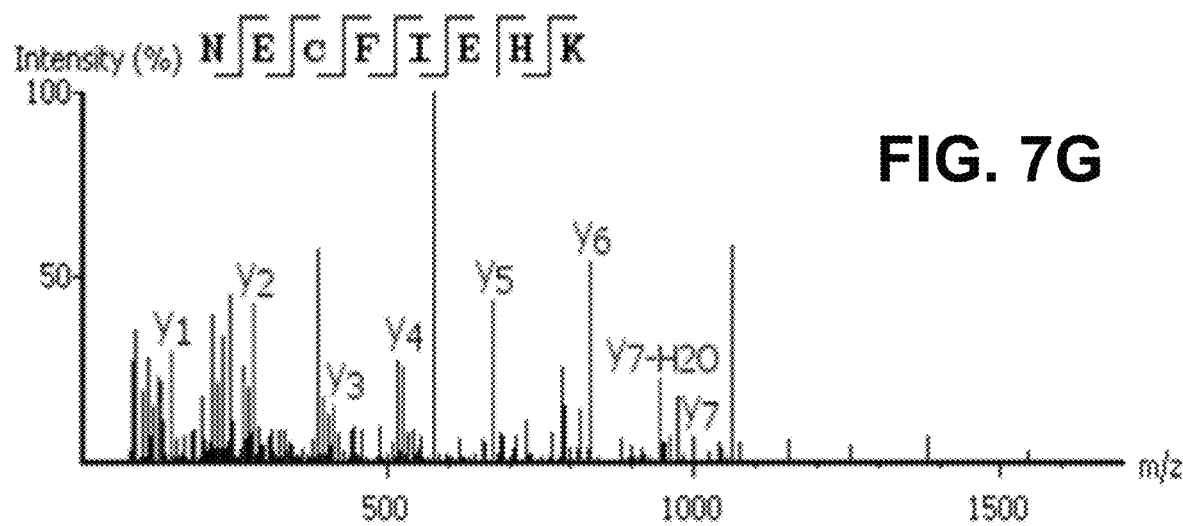
Figure 7H:
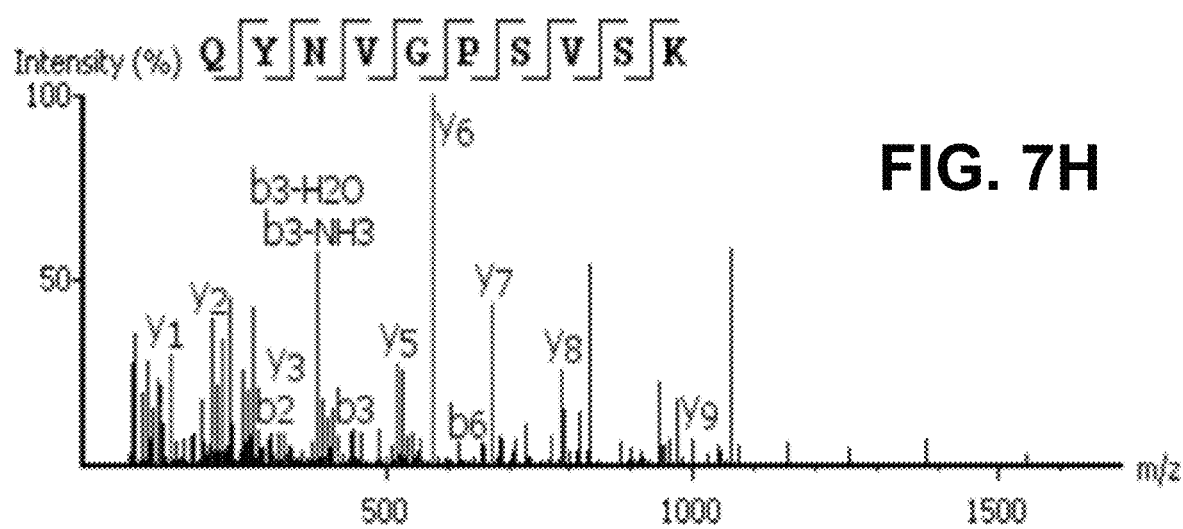
Figure 7I:
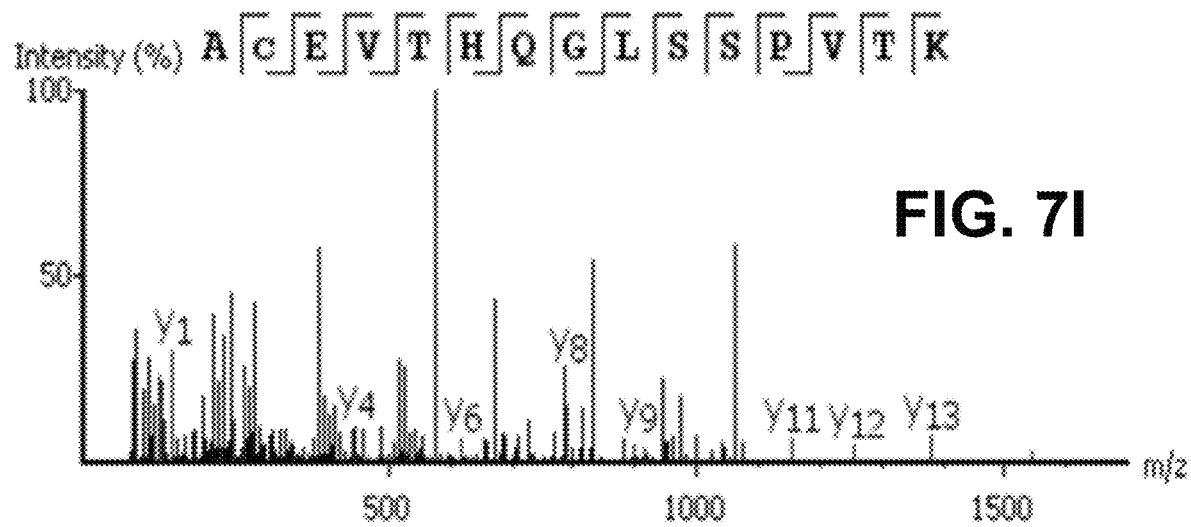

Turning to FIGS. 7g, 7h, and 7i, the systems provided herein identified all three different peptides using a DIA spectrum from the plasma dataset that contained mixed fragment ions. The last two peptides (FIGS. 7h and 7i) were predicted by both DeepNovo and the database search, however, the first one (FIG. 7g) did not exist in a database and therefore could not be predicted using a database search. Accordingly, the combination of DIA and de novo sequencing is highly effective in discovering novel peptides and enabling profiling of a biological sample.

REFERENCES

1. Ott, P. A. et al. An immunogenic personal neoantigen vaccine for patients with melanoma. *Nature* 547, 217-221 (2017).
2. Sahin, U. et al. Personalized RNA mutanome vaccines mobilize poly-specific therapeutic immunity against cancer. *Nature* 547, 222-226 (2017).
3. Editorial. The problem with neoantigen prediction. *Nat. Biotechnol.* 35, 97 (2017).
4. Vitiello, A. & Zanetti, M. Neoantigen prediction and the need for validation. *Biotechnol.* 35, 815-817 (2017).
5. Bassani-Sternberg, M. et al. Direct identification of clinically relevant neoepitopes presented on native human melanoma tissue by mass spectrometry. *Nat. Commun.* 7, 13404 (2016).
6. Venable, J. D., Dong, M. Q., Wohlschlegel, J., Dillin, A. & Yates, J. R. Automated approach for quantitative analysis of complex peptide mixtures from tandem mass spectra. *Nat. Methods* 1, 39-45 (2004).
7. Mist, H. L. et al. OpenSWATH enables automated, targeted analysis of data-independent acquisition MS data. *Nat. Biotechnol.* 32, 219-223 (2014).

8. Egertson, J. D., MacLean, B., Johnson, R., Xuan, Y. & MacCoss, M. J. Multiplexed peptide analysis using data-independent acquisition and Skyline. *Nat. Protoc.* 10, 887-903 (2015).
9. Tsou, C. et al. DIA-Umpire: comprehensive computational framework for data-independent acquisition proteomics. *Nat. Methods* 12, 258-264 (2015).
10. Ting, Y. S. et al. PECAN: library-free peptide detection for data-independent acquisition tandem mass spectrometry data. *Nat. Methods* 14, 903-904 (2017).
11. Tran, N. H, Zhang, X., Xin, L., Shan, B. & Li, M. De novo peptide sequencing by 219 deep learning. *Proc. Natl. Acad. Sci. U.S.A.* 114, 8247-8252 (2017).
12. Lin, T. Y., Goyal, P., Girshick, R., He, K. & Dollar, P. Focal loss for dense object 221 detection. arXiv: 1708.02002 [cs.CV] (2017).222
13. Zhang, J. et al. PEAKS DB: De novo sequencing assisted database search for 223 sensitive and accurate peptide identification. *Mol. Cell. Proteomics* 11, 224 M111.010587 (2012).225
14. Muntel, J. et al. Advancing urinary protein biomarker discovery by data-226 independent acquisition on a Quadrupole-Orbitrap mass spectrometer. *J.* 227 *Proteome Res.* 14, 4752-4762 (2015).228
15. Tan, J. et al. A LAIR1 insertion generates broadly reactive antibodies against 229 malaria variant antigens. *Nature* 529, 105-109 (2016).230
16. Bernhardt, O. et al. Spectronaut: a fast and efficient algorithm for MRM-like 231 processing of data independent acquisition (SWATH-MS) data. 60th American 232 Society for Mass Spectometry Conference (2012).
17. Caron, E. et al. An open-source computational and data resource to analyze 234 digital maps of immunopeptidomes. *eLife* 4, e07661 (2015).

The invention claimed is:

1. A computer implemented system for de novo sequencing of a peptide from mass spectrometry data acquired by data-independent acquisition using neural networks, the computer implemented system comprising:
at least one memory and at least one processor configured to receive:
a first input representing at least one precursor profile, each precursor profile representing intensities of one or more precursor ion signals associated with a precursor retention time;
a second input representing a plurality of fragment ion spectra for each precursor profile, each fragment ion spectra representing:
signals from fragment ions generated from an associated precursor ion, and
a fragment retention time; and
provide a plurality of layered computing nodes configured to form an artificial neural network for generating a probability measure for one or more candidates to a next amino acid in an amino acid sequence, the artificial neural network trained on mass spectrometry data containing retention time, a plurality of fragment ions peaks of sequences differing in length and differing by one or more amino acids;
wherein the plurality of layered nodes are configured to receive a mass spectrometry spectrum data base on the first and second inputs, the mass spectrometry spectrum data representing the at least one precursor profile and the fragment ion spectra, the plurality of layered nodes comprising at least one convolutional layer for filtering mass spectrometry spectrum data to detect fragment ion peaks; and
wherein the processor is configured to:
receive an input prefix representing a determined amino acid sequence of the peptide,
provide the mass spectrometry spectrum data to the plurality of layered nodes,
identify a next amino acid based on a candidate next amino acid having a greatest probability measure based on the output of the artificial neural network and the mass spectrometry spectrum data of the peptide;
update the determined amino acid sequence with the next amino acid,
and generate an output signal representing a final determined sequence;
wherein the plurality of layered nodes receives a matrix data representing the mass spectrometry spectrum data, and output a probability measure vector; and wherein the second input comprises a matrix data representing:
i. batch size,
ii. number of amino acids;
iii. ion types;
iv. number of fragment ion spectra associated with a precursor profile; and
v. window size for filtering fragment ion peaks.

2. The system of claim 1, wherein the plurality of fragment ion spectra comprise at most ten fragment ion spectra selected based on having fragment retention times that are closest to the precursor retention time.

3. The system of claim 2, comprising five fragment ion spectra for each precursor ion.

4. The system of claim 1, wherein the plurality of layered nodes receives the first and second inputs in parallel.

5. The system of claim 4, wherein the plurality of layered nodes comprising the at least one convolutional layer is for filtering the second input.

6. The system of claim 5, comprising 2 or 3 convolutional layers.

7. The system of claim 6, comprising 3 convolutional layers.

8. The system of claim 5, wherein the plurality of layered nodes comprise a first fully-connected layer having as many neuron units as there are outputs from the at least one convolutional layer, and a second fully-connected layer comprising as many neuron units as there are possible entries for the next amino acid.

9. The system of claim 1, wherein the plurality of layered nodes comprise at least one fully-connected layer for identifying pairs of:
a) a fragment ion peak corresponding to a sequence that is one amino acid longer than the determined amino acid sequence, and
b) a fragment ion peak corresponding to a sequence that is one amino acid less than the remaining undetermined amino acid sequence of the peptide,
by fitting the plurality of fragment ions peaks against the mass spectrometry spectrum data, and for outputting the probability measure for each candidate next amino acid.

10. The system of claim 9, wherein a pair of fragment ion peaks are filtered out when the sum of:
a mass corresponding to the fragment ion peak of a), and
a mass corresponding to the fragment ion peak of b)
exceed the total mass of the peptide.

11. The system of claim 1, comprising a mass spectrometer configured to generate a mass spectrometry spectrum data of a peptide.

12. The system of claim 1, wherein the processor is configured to apply a focal loss function to obtain the probability measures of candidates.

13. The system of claim 1, wherein the processor is configured to determine the sequence of the peptide by obtaining the probability measures of candidates at a number of points in the sequence and beam searching.

14. The system of claim 1, wherein the system is configured to bi-directionally sequence the peptide using two separate sets of parameters, wherein one set comprises parameters for forward sequencing and the other set comprises parameters for backward sequencing.

15. The system of claim 1, wherein the artificial neural network is further trained on a database of peptide sequences; and
wherein the plurality of layered nodes comprise:
one or more layers comprising a convolutional neural network (CNN) for identifying the presence of amino acids in the mass spectrometry spectrum data and generate one or more output vectors representing a list of amino acids present in the peptide; and
one or more layers comprising a recurrent neural network (RNN) for predicting the next amino acid by vector embedding the one or more output vectors, and for outputting the probability measure for each candidate next amino acid.

16. The system of claim 15, wherein the one or more layers of the plurality of layered nodes comprising the RNN is a long short-term memory network (LSTM).

17. The system of claim 15, wherein the one or more layers comprising the CNN is for identifying the presence of amino acids in the mass spectrometry spectrum data by fitting single or multiple amino acid long fragment ion peaks to the mass spectrometry spectrum data.

18. The system of claim 15, wherein the one or more layers comprising the CNN is for identifying the presence of amino acids in the mass spectrometry spectrum data by identifying two fragment ion peaks that differ by one amino acid.

19. A method for de novo sequencing of a peptide from mass spectrometry data acquired by data-independent acquisition using neural networks, the method comprising:
receiving a first input representing at least one precursor profile, each precursor profile representing intensities of one or more precursor ion signals associated with a precursor retention time;
receiving a second input representing a plurality of fragment ion spectra for each precursor profile, each fragment ion spectra representing:
signals from fragment ions generated from an associated precursor ion, and
a fragment retention time;
filtering the mass spectrometry spectrum data to detect fragment ion peaks by at least one convolutional layer of a plurality of layered nodes configured to form an artificial neural network for generating a probability measure for one or more candidates to a next amino acid in an amino acid sequence;
receiving a probability measure for each candidate of a next amino acid;
obtaining an input prefix representing a determined amino acid sequence of the peptide;
providing a mass spectrometry spectrum data based on the first and second inputs to the plurality of layered nodes;
identifying a next amino acid based on a candidate next amino acid having a greatest probability measure based on the output of the artificial neural network and the mass spectrometry spectrum data of the peptide;
updating the determined amino acid sequence with the next amino acid; and
generating an output signal representing a final determined sequence;
wherein the plurality of layered nodes receives a matrix data representing the mass spectrometry spectrum data, and output a probability measure vector; and wherein the second input comprises a matrix data representing:
a) batch size,
b) number of amino acids;
c) ion types;
d) number of fragment ion spectra associated with a precursor profile; and
e) window size for filtering fragment ion peaks.

20. The method of claim 19, wherein the plurality of layered nodes receives the first and second inputs in parallel.

21. The method of claim 19, comprising fitting a plurality of fragment ions peaks of sequences against the mass spectrometry spectrum data to identifying pairs of:
a) a fragment ion peak corresponding to a sequence that is one amino acid longer than the determined amino acid sequence, and
b) a fragment ion peak corresponding to a sequence that is one amino acid less than the remaining undetermined amino acid sequence of the peptide,
by at least one fully-connected layer of the plurality of layered nodes.

22. The method of claim 21, wherein the fragment ion peaks of sequences differ in length and differ by one or more amino acids, and wherein the method comprises training the artificial neural network on the fragment ion peaks.

23. The method of claim 21, comprising filtering out a pair of fragment ion peaks when the sum of:
a mass corresponding to the fragment ion peak of a), and
a mass corresponding to the fragment ion peak of b)
exceed the total mass of the peptide.

24. The method of claim 19, comprising:
identifying the presence of amino acids in the mass spectrometry spectrum data by one or more layers of the plurality of layered nodes comprising a convolutional neural network;
generating one or more output vectors representing a list of amino acids present in the peptide;
predicting a next amino acid by vector embedding the one or more output vectors by one or more layers of the plurality of layered nodes comprising a recurrent neural network.

25. The method of claim 24, comprising training the plurality of layered nodes on:
mass spectrometry spectrum data containing a plurality of fragment ions of sequences differing in length and differing by one or more amino acids, and
a database of peptide sequences.

26. The method of claim 24, comprising identifying the presence of amino acids in the mass spectrometry spectrum data by fitting single or multiple amino acid long fragment ion peaks to the mass spectrometry spectrum data.

27. The method of claim 24, comprising identifying the presence of amino acids in the mass spectrometry spectrum data by identifying two fragment ion peaks that differ by one amino acid.

28. A non-transitory computer readable media storing machine interpretable instructions, which when executed, cause a processor to perform steps of a method comprising:

receiving a first input representing at least one precursor profile, each precursor profile representing intensities of one or more precursor ion signals associated with a precursor retention time;

receiving a second input representing a plurality of fragment ion spectra for each precursor profile, each fragment ion spectra representing:

signals from fragment ions generated from an associated precursor ion, and a fragment retention time;

filtering the mass spectrometry spectrum data to detect fragment ion peaks by at least one convolutional layer of a plurality of layered nodes configured to form an artificial neural network for generating a probability measure for one or more candidates to a next amino acid in an amino acid sequence;

receiving a probability measure for each candidate of a next amino acid;

obtaining an input prefix representing a determined amino acid sequence of the peptide;

providing a mass spectrometry spectrum data based on the first and second inputs to the plurality of layered nodes;

identifying a next amino acid based on a candidate next amino acid having a greatest probability measure based on the output of the artificial neural network and the mass spectrometry spectrum data of the peptide;

updating the determined amino acid sequence with the next amino acid; and generating an output signal representing a final determined sequence;

wherein the plurality of layered nodes receives a matrix data representing the mass spectrometry spectrum data, and output a probability measure vector; and wherein the second input comprises a matrix data representing:

a) batch size,
b) number of amino acids;
c) ion types;
d) number of fragment ion spectra associated with a precursor profile; and
e) window size for filtering fragment ion peaks.

29. The non-transitory computer readable media of claim 28, wherein the plurality of layered nodes receives the first and second inputs in parallel.

30. The non-transitory computer readable media of claim 28, the method comprising fitting a plurality of fragment ions peaks of sequences against the mass spectrometry spectrum data to identifying pairs of:

a) a fragment ion peak corresponding to a sequence that is one amino acid longer than the determined amino acid sequence, and b) a fragment ion peak corresponding to a sequence that is one amino acid less than the remaining undetermined amino acid sequence of the peptide, by at least one fully-connected layer of the plurality of layered nodes.

31. The non-transitory computer readable media of claim 30, wherein the fragment ion peaks of sequences differ in length and differ by one or more amino acids, and wherein the method comprises training the artificial neural network on the fragment ion peaks.

32. The non-transitory computer readable media of claim 30, the method comprising filtering out a pair of fragment ion peaks when the sum of:

a mass corresponding to the fragment ion peak of a), and a mass corresponding to the fragment ion peak of b) exceed the total mass of the peptide.

33. The non-transitory computer readable media of claim 28, the method comprising:

identifying the presence of amino acids in the mass spectrometry spectrum data by one or more layers of the plurality of layered nodes comprising a convolutional neural network;

generating one or more output vectors representing a list of amino acids present in the peptide;

predicting a next amino acid by vector embedding the one or more output vectors by one or more layers of the plurality of layered nodes comprising a recurrent neural network.

34. The non-transitory computer readable media of claim 33, the method comprising training the plurality of layered nodes on:

mass spectrometry spectrum data containing a plurality of fragment ions of sequences differing in length and differing by one or more amino acids, and a database of peptide sequences.

35. The non-transitory computer readable media of claim 33, the method comprising identifying the presence of amino acids in the mass spectrometry spectrum data by fitting single or multiple amino acid long fragment ion peaks to the mass spectrometry spectrum data.

36. The non-transitory computer readable media of claim 33, the method comprising identifying the presence of amino acids in the mass spectrometry spectrum data by identifying two fragment ion peaks that differ by one amino acid.

* * * * *